(12) United States Patent
Wersland et al.

(10) Patent No.: US 11,432,994 B2
(45) Date of Patent: Sep. 6, 2022

(54) INTELLIGENCE ENGINE SYSTEM AND METHOD

(71) Applicant: Therabody, Inc., Los Angeles, CA (US)

(72) Inventors: Jason Wersland, Manhattan Beach, CA (US); Benjamin Nazarian, Beverly Hills, CA (US); Jaime Sanchez Solana, Los Angeles, CA (US); Eduardo Merino, Beverly Hills, CA (US); Gregory L. Chambers, Beverly Hills, CA (US); Daniel Delshad, Beverly Hills, CA (US); Timothy Roberts, Beverly Hills, CA (US)

(73) Assignee: Therabody, Inc., Los Angeles, CA (US)

(*) Notice: Subject to any disclaimer, the term of this patent is extended or adjusted under 35 U.S.C. 154(b) by 0 days.

(21) Appl. No.: 17/066,230

(22) Filed: Oct. 8, 2020

(65) Prior Publication Data
US 2021/0022955 A1 Jan. 28, 2021

Related U.S. Application Data

(63) Continuation-in-part of application No. 16/869,389, filed on May 7, 2020, now Pat. No. 10,959,911,
(Continued)

(51) Int. Cl.
*A61H 23/00* (2006.01)
*A61B 5/0205* (2006.01)
(Continued)

(52) U.S. Cl.
CPC ....... *A61H 23/006* (2013.01); *A61B 5/02055* (2013.01); *A61B 5/1118* (2013.01);
(Continued)

(58) Field of Classification Search
CPC .......... A61H 1/00; A61H 1/006; A61H 1/008; A61H 23/00; A61H 23/004; A61H 23/006;
(Continued)

(56) References Cited

U.S. PATENT DOCUMENTS 1,545,027 A 7/1925 Ashlock
1,657,765 A 1/1928 Pasque
(Continued)

FOREIGN PATENT DOCUMENTS

CN 2788807 6/2006
CN 201524220 U 7/2010
(Continued)

OTHER PUBLICATIONS

PCT/US2016/038326 International Search Report & Written Opinion dated Sep. 1, 2016.
(Continued)

*Primary Examiner* — Colin W Stuart
(74) *Attorney, Agent, or Firm* — Sterne, Kessler, Goldstein & Fox P.L.L.C.

(57) ABSTRACT

A percussive therapy system that includes a percussive massage device including a network interface, and an intelligence engine. The intelligence engine is configured to receive manual capture data and real-time tracking data from the percussive massage device, receive remote data from a remote data source, and generate recommendation data comprising a recommended protocol to be performed by the percussive massage device. The recommendation data is generated from demographic, activity, temporal, analytics, and biometric data, received from the manual capture data, the real-time tracking data, and the remote data inputs.

17 Claims, 31 Drawing Sheets

Related U.S. Application Data which is a continuation-in-part of application No. 16/796,143, filed on Feb. 20, 2020, now Pat. No. 10,940,081, application No. 17/066,230, filed on Oct. 8, 2020, which is a continuation-in-part of application No. 16/675,772, filed on Nov. 6, 2019, now Pat. No. 10,702,448.

(60) Provisional application No. 62/899,098, filed on Sep. 11, 2019, provisional application No. 62/912,392, filed on Oct. 8, 2019, provisional application No. 62/785,151, filed on Dec. 26, 2018.

(51) Int. Cl.
| | |
|---|---|
| *A61B 5/00* | (2006.01) |
| *A61B 6/00* | (2006.01) |
| *A61B 8/00* | (2006.01) |
| *A61B 5/11* | (2006.01) |
| *G16H 20/30* | (2018.01) |
| *G16H 50/30* | (2018.01) |
| *A61H 23/02* | (2006.01) |
| *A61B 5/024* | (2006.01) |
| *A61B 5/01* | (2006.01) |

(52) U.S. Cl.
CPC ............ *A61B 5/486* (2013.01); *A61B 5/4806* (2013.01); *A61B 6/00* (2013.01); *A61B 8/00* (2013.01); *G16H 20/30* (2018.01); *G16H 50/30* (2018.01); *A61B 5/015* (2013.01); *A61B 5/02405* (2013.01); *A61H 23/0263* (2013.01); *A61H 2201/5012* (2013.01); *A61H 2201/5043* (2013.01); *A61H 2201/5058* (2013.01); *A61H 2201/5097* (2013.01); *A61H 2230/065* (2013.01); *A61H 2230/505* (2013.01); *A61H 2230/805* (2013.01); *A61H 2230/825* (2013.01)

(58) Field of Classification Search
CPC ............... A61H 23/02; A61H 23/0218; A61H 23/0254; A61H 23/0263; A61H 23/04; A61H 23/06; A61H 2023/002; A61H 2023/0209; A61H 2023/0272; A61H 2023/0281; A61H 2023/029; A61H 39/00; A61H 39/002; A61H 39/007; A61H 39/04; A61H 2201/0165; A61H 2201/12; A61H 2201/1207; A61H 2201/1215; A61H 2201/1223; A61H 2201/123; A61H 2201/1238; A61H 2201/14; A61H 2201/1409; A61H 2201/1418; A61H 2201/1481; A61H 2201/149; A61H 2201/1664; A61H 2201/50; A61H 2201/5007; A61H 2201/501; A61H 2201/5012; A61H 2201/5035; A61H 2201/5058; A61H 2201/5097; A61H 2230/04; A61H 2230/045; A61H 2230/06; A61H 2230/065; A61H 2230/08; A61H 2230/085; A61H 2230/30; A61H 2230/305; A61H 2230/50; A61H 2230/505; A61H 2230/70; A61H 2230/705; A61H 2230/80; A61H 2230/805; A61H 2230/82; A61H 2230/825; G16H 20/30; G16H 50/30; A61B 5/1118; A61B 5/02405; A61B 5/4806; A61B 5/486; A61B 5/015
See application file for complete search history.

(56) References Cited

U.S. PATENT DOCUMENTS

| | | |
|---|---|---|
| D91,454 S | 2/1934 | Decker |
| D93,943 S | 11/1934 | Rand |
| D118,980 S | 2/1940 | Larson |
| D129,045 S | 8/1941 | Wilhide |
| D161,484 S | 1/1951 | McQuown |
| D163,324 S | 5/1951 | Rittenhouse |
| D180,923 S | 9/1957 | Anton |
| D181,742 S | 12/1957 | Madl |
| 2,931,632 A | 4/1960 | Angelis |
| D195,145 S | 4/1963 | Ernest |
| D197,142 S | 12/1963 | Godfrey |
| 3,172,675 A | 3/1965 | Gonzalez |
| D207,505 S | 4/1967 | Whitman |
| 3,452,226 A | 6/1969 | Hettich |
| 3,545,301 A | 12/1970 | Richter |
| 3,626,934 A | 12/1971 | Andis |
| D237,454 S | 11/1975 | Adams |
| D237,455 S | 11/1975 | Schramm |
| 3,942,251 A | 3/1976 | Griffies |
| 4,150,668 A | 4/1979 | Johnston |
| 4,173,217 A | 11/1979 | Johnston |
| D265,985 S | 8/1982 | House |
| 4,549,535 A | 10/1985 | Wing |
| 4,566,442 A | 1/1986 | Mabuchi |
| D287,814 S | 1/1987 | Hiraishi |
| D292,368 S | 10/1987 | Mikiya |
| 4,730,605 A | 3/1988 | Noble et al. |
| D300,132 S | 3/1989 | Culbertson |
| 4,815,224 A | 3/1989 | Miller |
| D303,373 S | 9/1989 | Ching, Jr. |
| D310,005 S | 8/1990 | Precht |
| D314,320 S | 2/1991 | Brosius |
| D320,379 S | 10/1991 | Culbertson |
| D321,338 S | 11/1991 | Sakamoto |
| 5,085,207 A | 2/1992 | Fiore |
| D329,166 S | 9/1992 | Doggett |
| D329,291 S | 9/1992 | Wollman |
| D334,012 S | 3/1993 | Chen |
| 5,212,887 A | 5/1993 | Farmerie |
| D338,802 S | 8/1993 | Maass |
| D345,077 S | 3/1994 | Maass |
| D345,727 S | 4/1994 | Flowers |
| D345,888 S | 4/1994 | Joss |
| D349,029 S | 7/1994 | Matsunaga |
| 5,417,644 A | 5/1995 | Lee et al. |
| D363,352 S | 10/1995 | Huen |
| D367,712 S | 3/1996 | Young |
| D374,934 S | 10/1996 | Lie |
| 5,569,168 A | 10/1996 | Hartwig |
| 5,573,500 A | 11/1996 | Katsunuma |
| D383,366 S | 9/1997 | Heck |
| D383,435 S | 9/1997 | Svetlik |
| D384,639 S | 10/1997 | Kawakami |
| D387,728 S | 12/1997 | Kawakami |
| D388,175 S | 12/1997 | Lie |
| D397,991 S | 9/1998 | Kawakami |
| D400,161 S | 10/1998 | Nagele |
| D400,758 S | 11/1998 | Hippen |
| D412,485 S | 8/1999 | Kato |
| 5,951,501 A | 9/1999 | Griner |
| D417,648 S | 12/1999 | Clowers |
| D425,014 S | 5/2000 | Willkens |
| D430,774 S | 9/2000 | Naft |
| D432,077 S | 10/2000 | Zurwelle |
| D433,300 S | 11/2000 | Buck |
| D440,136 S | 4/2001 | Buck |
| 6,228,042 B1 | 5/2001 | Dungan |
| D474,445 S | 5/2003 | Matsuoka |
| D475,595 S | 6/2003 | Hatch |
| D475,679 S | 6/2003 | Cooper |
| D476,746 S | 7/2003 | Harris |
| 6,599,260 B2 | 7/2003 | Tucek |
| D478,385 S | 8/2003 | Dirks |
| D481,279 S | 10/2003 | Buck |
| 6,663,657 B1 | 12/2003 | Miller |

(56) References Cited

U.S. PATENT DOCUMENTS

| | | |
|---|---|---|
| 6,682,496 B1 | 1/2004 | Pivaroff |
| 6,723,060 B2 | 4/2004 | Miller |
| D504,111 S | 4/2005 | Ozawa |
| D510,317 S | 10/2005 | Sun |
| D530,270 S | 10/2006 | Ozawa |
| D531,733 S | 11/2006 | Burout |
| D544,102 S | 6/2007 | Pivaroff |
| D544,436 S | 6/2007 | Kawahara |
| D547,264 S | 7/2007 | Kondo |
| D553,562 S | 10/2007 | Okada |
| D575,224 S | 8/2008 | Taniguchi |
| D579,868 S | 11/2008 | Harrison |
| D580,353 S | 11/2008 | Harrison |
| D587,977 S | 3/2009 | Waldron |
| D593,204 S | 5/2009 | Manke |
| D597,482 S | 8/2009 | Kondo |
| D604,235 S | 11/2009 | Tarter |
| D605,586 S | 12/2009 | Tong |
| D622,660 S | 8/2010 | Taniguchi |
| D631,315 S | 1/2011 | Xue |
| 7,927,259 B1 | 4/2011 | Rix |
| 7,996,996 B2 | 8/2011 | Hirabayashi |
| D666,303 S | 8/2012 | Ding |
| 8,342,187 B2 | 1/2013 | Kalman |
| D682,195 S | 5/2013 | Aglassinger |
| 8,646,348 B2 | 2/2014 | Hung |
| D703,480 S | 4/2014 | Lownds |
| D722,016 S | 2/2015 | Beukema |
| 8,951,216 B2 | 2/2015 | Yoo et al. |
| D726,495 S | 4/2015 | Ryan |
| D740,222 S | 10/2015 | Tang |
| D776,612 S | 1/2017 | Chen |
| D817,869 S | 5/2018 | Lee |
| D826,418 S | 8/2018 | Lad |
| 10,201,470 B2 | 2/2019 | Griner |
| D842,489 S | 3/2019 | Spewock |
| 10,276,844 B2 | 4/2019 | Wackwitz |
| 10,314,762 B1* | 6/2019 | Marton ............... A61H 23/004 |
| D855,822 S | 8/2019 | Marton |
| D858,432 S | 9/2019 | Altenburger |
| D862,382 S | 10/2019 | Altenburger |
| D866,790 S | 11/2019 | Lee |
| D867,279 S | 11/2019 | Altenburger |
| D877,351 S | 3/2020 | Wersland |
| D884,205 S | 5/2020 | Zhuang |
| D893,738 S | 8/2020 | Zhuang |
| D919,560 S | 5/2021 | Taniguchi |
| 2001/0016697 A1 | 8/2001 | Gorsen |
| 2003/0009116 A1 | 1/2003 | Luettgen |
| 2003/0094356 A1 | 5/2003 | Waldron |
| 2003/0144615 A1 | 7/2003 | Lin |
| 2003/0195443 A1 | 10/2003 | Miller |
| 2006/0025710 A1 | 2/2006 | Schulz |
| 2006/0123941 A1 | 6/2006 | Wadge |
| 2006/0192527 A1 | 8/2006 | Kageler |
| 2007/0144310 A1 | 6/2007 | Pozgay |
| 2007/0150004 A1 | 6/2007 | Colloca |
| 2007/0270727 A1 | 11/2007 | Khorassani Zadeh |
| 2008/0103419 A1 | 5/2008 | Adamson |
| 2008/0314610 A1 | 12/2008 | Meixner |
| 2012/0253245 A1 | 10/2012 | Stanbridge |
| 2013/0133210 A1 | 5/2013 | Weir |
| 2013/0138023 A1 | 5/2013 | Lerro |
| 2013/0261516 A1 | 10/2013 | Cilea |
| 2013/0281897 A1 | 10/2013 | Hoffmann |
| 2014/0024982 A1 | 1/2014 | Doyle |
| 2014/0180331 A1 | 6/2014 | Turner |
| 2015/0005682 A1 | 1/2015 | Danby |
| 2015/0119771 A1 | 4/2015 | Roberts |
| 2015/0148592 A1 | 5/2015 | Kanbar |
| 2015/0375315 A1 | 12/2015 | Ukai |
| 2016/0129186 A1* | 5/2016 | Douglas ............... G16H 40/67 601/84 |
| 2016/0166464 A1* | 6/2016 | Douglas ............... A61H 9/0078 601/148 |
| 2016/0367425 A1 | 12/2016 | Wersland |
| 2017/0069191 A1* | 3/2017 | Erkkila ............... G08B 21/043 |
| 2017/0156974 A1 | 6/2017 | Griner |
| 2017/0312161 A1* | 11/2017 | Johnson ............... A61H 1/006 |
| 2018/0133101 A1* | 5/2018 | Inada ............... G10L 15/26 |
| 2018/0200141 A1 | 7/2018 | Wersland |
| 2018/0236572 A1 | 8/2018 | Ukai |
| 2018/0243158 A1 | 8/2018 | Loghmani |
| 2018/0279843 A1 | 10/2018 | Paul |
| 2018/0296433 A1 | 10/2018 | Danby |
| 2018/0315499 A1* | 11/2018 | Appelbaum ............ G16H 10/20 |
| 2018/0315504 A1* | 11/2018 | Inada ............... A61B 5/0053 |
| 2019/0314239 A1* | 10/2019 | Ci ............... A61H 7/00 |
| 2019/0381271 A1* | 12/2019 | Jo ............... G06K 9/00228 |
| 2020/0016027 A1* | 1/2020 | Kim ............... A61H 7/007 |

FOREIGN PATENT DOCUMENTS

| | | |
|---|---|---|
| CN | 201743890 U | 2/2011 |
| CN | 201847899 U | 6/2011 |
| CN | 203598194 U | 5/2014 |
| CN | 104352341 | 7/2016 |
| JP | 1990019157 | 1/1990 |
| JP | 1992047440 | 4/1992 |
| JP | 1995051393 | 2/1995 |
| JP | 003077837 | 6/2001 |
| JP | 2005204777 | 4/2005 |
| JP | 2010534110 | 11/2010 |
| KR | 200313149 Y1 | 5/2003 |
| KR | 101123926 | 4/2012 |
| KR | 101406275 | 6/2014 |
| TW | 201440753 A | 8/2015 |
| WO | 2009014727 | 1/2009 |
| WO | 2014118596 | 8/2014 |
| WO | 2015038005 | 3/2015 |

OTHER PUBLICATIONS

PCT/US2018/022426 International Search Report & Written Opinion dated May 31, 2018.
AU 2016284030 Examination Report dated May 7, 2018.
JP2018-517683 Office Action dated Oct. 25, 2018.
CA 2990178 Office Action dated Oct. 25, 2018.
WORX Trans4mer "Safety and Operating Manual Original Instructions" for 12V Li-Ion Multi-purpose saw, WX540, WX540.3, WX540.9, 2013.
Rachel [no family name indicated], "Jigsaw Massager", Apr. 18, 2010 (https://web.archive.org/web/20100418041422/http://www.instructables.com/id/Jigsaw-Massager/).
Rockwell Trans4mer Operating Manual for Multi-purpose saw, Model RK2516/RK2516K, 2011.
PCT/US2020/031936 International Search Report & Written Opinion dated Sep. 11, 2020.
TheraGun device in YouTube video "TheraGun: What It Does," https://www.youtube.com/watch?v=FB_JTZnD7vs; Aug. 24, 2016 (upload date).
TheraGun device in Archive.org webpage https://web.archive.org/web/20151218063848/http://www.theragun.com/#intro-1 Dec. 18, 2015 (archive date).
TheraGun G1 device in YouTube video "Theragun G1: Product Overview," https://www.youtube.com/watch?v=m9ilhfMGfZ8 Apr. 18, 2017 (upload date).
TheraGun G2Pro device in YouTube video "The Theragun G2PRO: Revolutionary Percussive Therapy," https://www.youtube.com/watch?v=2p9R6VA798o Oct. 10, 2017 (upload date).

* cited by examiner

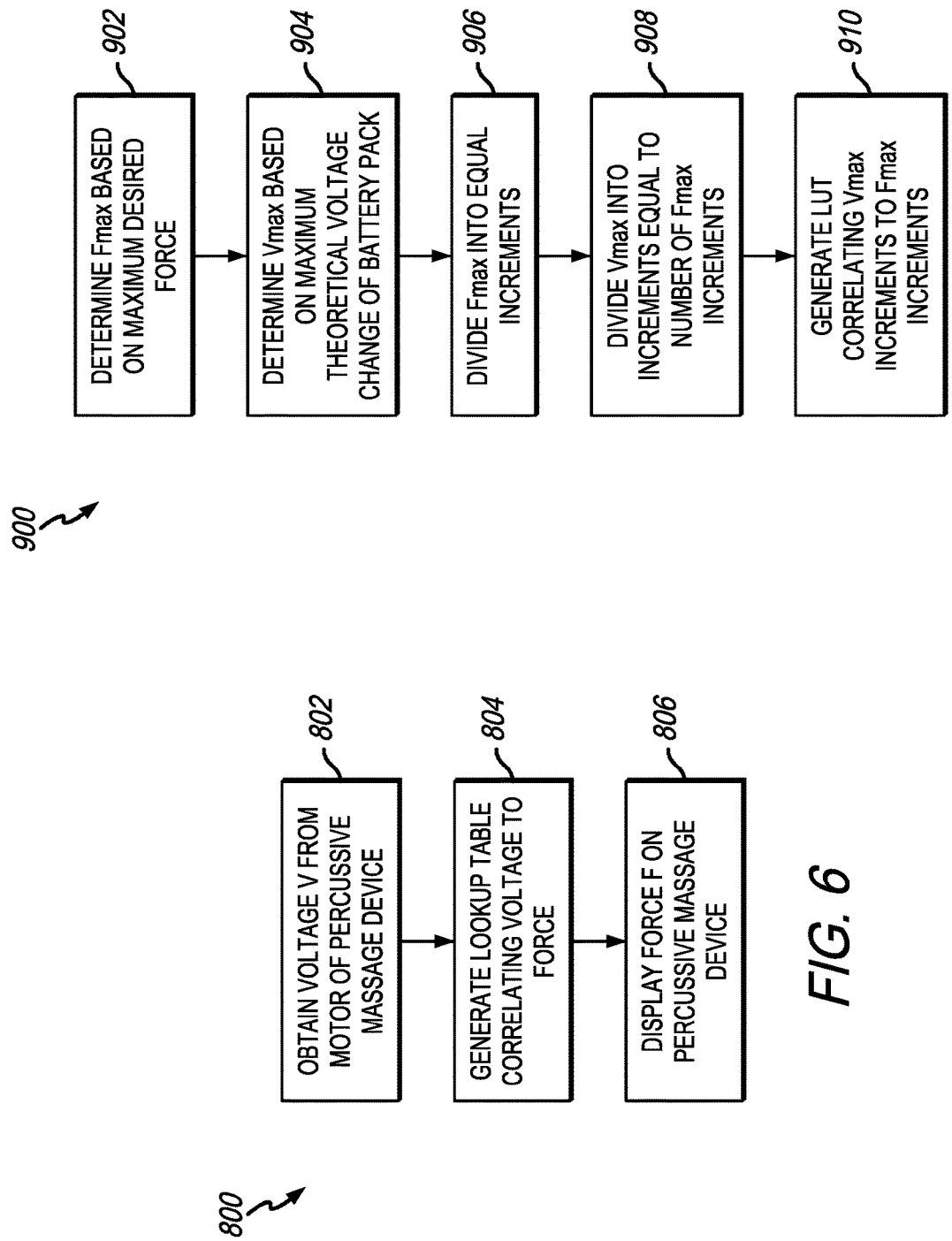

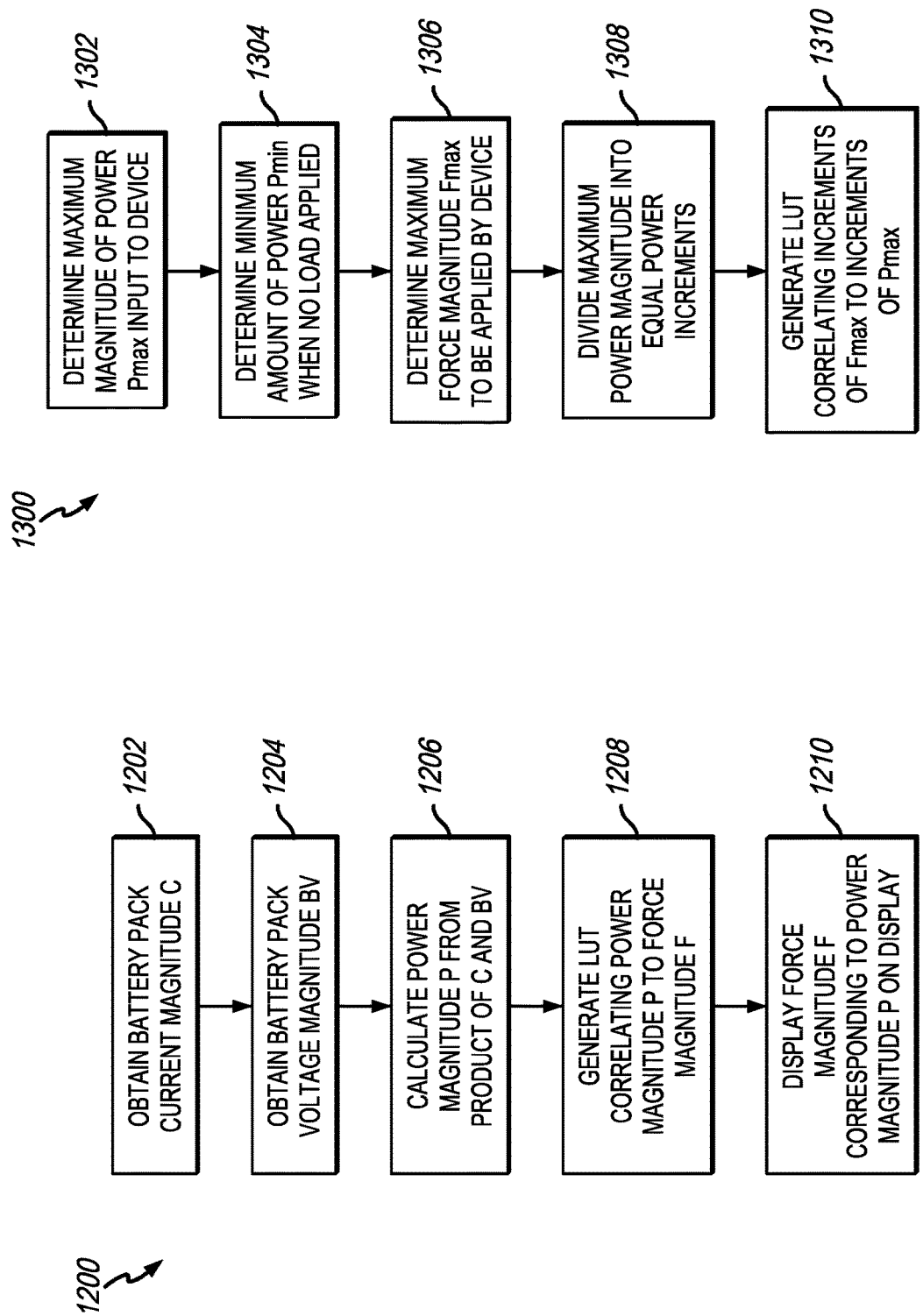

| | PROTOCOL 1 | | | |
|---|---|---|---|---|
| STEP | 1 | 2 | 3 | 4 |
| TIME(M) | 0:30 | 0:15 | 0:30 | 0:45 |
| SPEED (RPM) | 1550 | 2100 | 2200 | 2400 |
| AMPLITUDE | 2 | 3 | 1 | 4 |
| ATTACHMENT | DAMPENER | SMALL BALL | DAMPENER | LARGE BALL |
| FORCE | 1 | 3 | 3 | 2 |
| TEMPERATURE (°C) | 21 | 26 | 29 | 32 |
| GRIP | 1 | 1 | 1 | 1 |

*FIG. 25*

PROTOCOL: SHIN SPLINTS

| STEP | 1 | 2 | 3 | 4 |
|---|---|---|---|---|
| TIME(M) | 1:00 | 1:00 | 1:00 | 1:00 |
| SPEED (RPM) | 1500 | 1500 | 2000 | 2000 |
| AMPLITUDE | 1 | 1 | 3 | 3 |
| ATTACHMENT | DAMPENER | DAMPENER | DAMPENER | DAMPENER |
| FORCE | 2 | 2 | 3 | 3 |
| TEMPERATURE (°C) | 21 | 21 | 24 | 24 |
| GRIP | REVERSE | REVERSE | BASE | BASE |
| ARM POSITION | 1 | 1 | 1 | 1 |
| BODY PART | R. SHIN | L. SHIN | R. CALF | L. CALF |

FIG. 26

INTELLIGENCE ENGINE SYSTEM AND METHOD

CROSS-REFERENCE TO RELATED APPLICATIONS

This application is a continuation-in-part of U.S. patent application Ser. No. 16/869,389, filed May 7, 2020, which is a continuation-in-part of U.S. patent application Ser. No. 16/796,143, filed Feb. 20, 2020, which claims the benefit of U.S. Provisional Application No. 62/912,392, filed Oct. 8, 2019, U.S. Provisional Application No. 62/899,098, filed Sep. 11, 2019 and U.S. Provisional Application No. 62/844,424, filed May 7, 2019. This application is also a continuation-in-part of U.S. patent application Ser. No. 16/675,772, filed Nov. 6, 2019, now U.S. Pat. No. 10,702,448, which claims the benefit of U.S. Provisional Application No. 62/785,151, filed on Dec. 26, 2018. All applications listed above are incorporated by reference herein in their entireties.

FIELD OF THE INVENTION

The present invention relates generally to a system related to percussive massage devices.

BACKGROUND OF THE INVENTION

The background description disclosed anywhere in this patent application includes information that may be useful in understanding the present invention. It is not an admission that any of the information provided herein is prior art or relevant to the presently claimed invention, or that any publication specifically or implicitly referenced is prior art.

SUMMARY OF THE PREFERRED EMBODIMENTS

In accordance with a first aspect of the present invention, there is provided a percussive therapy system that includes a percussive massage device that includes a network interface, and an intelligence engine. The intelligence engine is configured to receive manual capture data and real-time tracking data from the percussive massage device, receive remote data from a remote data source, and generate recommendation data comprising a recommended protocol to be performed by the percussive massage device. The recommendation data is generated from demographic, activity, temporal, analytics, and biometric data, received from the manual capture data, the real-time tracking data, and the remote data inputs. The recommendation data may then be provided to the percussive massage device.

The recommendation data may be generated based at least in part on aggregated data from the manual capture data, the real-time tracking data, and the remote data inputs. The recommended protocol may include at least one step of a recommended routine, and may be particularized to a user of the device. The recommended protocol is configured to be particularized to a user of the percussive massage device based on demographic, activity, temporal, biometric, and imaging data. The recommended protocol may be modified by these data sources and may include a modification of steps in an exercise routine, inclusion or exclusion of a body part of a user in the exercise routine, duration of the routine, and frequency, force, and attachments utilized by the percussive massage device.

The recommendation data may include a behavior modification recommendation and a wellness insight, and may include a user notification of the recommended protocol, a change to the recommended protocol, and a behavior recommendation, and may be generated from a weighted scoring determination including a recovery determination score, a wellness determination score, and a behavior determination score. The recovery determination score may identify a measure of time before a user's heart rate has recovered from an exercise routine. The wellness determination score may assess sleep metrics and patterns of a user for a predetermined time period.

The demographic data may include a biological parameter of a user, an age of the user, a height of the user, and a weight of the user. The activity data may include a type of exercise activity, a volume of the exercise activity, an intensity of the exercise activity, and a trend in activity parameters over time. The volume of the exercise activity may include a distance, a time, and a number of repetitions. The intensity of the exercise activity may include a pace of the exercise activity or a load associated with the exercise activity. The temporal data may include an absolute time of an exercise routine of a user and a relative time of the exercise routine to a predetermined event. The analytics data may include a duration of use, a frequency of use, a force of use, and an attachment use of the percussive massage device. The analytics data may be particularized to a body part of a user. The biometric data may include a heart rate of a user, a heart rate variation of the user, sleep metrics of the user, and a temperature of the user. The biometric data may include a thermographic image of a user, an ultrasound of the user, and an x-ray image of the user.

A method of providing therapeutic effect using a percussive massage device includes receiving manual capture data and real-time tracking data of the percussive massage device, receiving remote data inputs from at least one remote data source, aggregating the manual capture data, the real-time tracking data, and the remote data inputs, each comprising at least one of demographic data, activity data comprising prior use of the percussive massage device, temporal data comprising timing of use of the percussive massage device, analytics data corresponding to use of the percussive massage device, and biometric data, and generating recommendation data from the aggregated data comprising a recommended protocol to be performed by the percussive massage device. The method may include providing the recommendation data to the percussive massage device.

In a preferred embodiment, the present invention includes a system and method for using artificial intelligence or other deep learning to determine the proper utilization of a percussive therapy device in the fitness, wellness, muscle recovery, and muscle activation setting. Another aspect of the invention includes a system for a given user's device learning how to work more effectively for that particular user. This system can apply to other fitness devices other than percussive massage devices. For example, if two subjects, a typical office worker and an NBA star each have a 10,000 step day, the 10,000 step day means something different to each of the subjects. In this situation, the present invention provides personalization and analyzes the different data provided by the two subjects. In a preferred embodiment, the present invention analyzes three different types of data, e.g., resistance a user had in previous activity that are applied in an algorithm. The user can then be informed how to use the device based on the results of the data analysis. For example, our office worker above may require recovery (use of the percussive massage device for a certain period of time) after the 10,000 steps and the NBA player may not.

In other words, the learning algorithm analyzes data and personalizes the percussive massage device recovery trends to the individual based on data gathered about the individual, what can be learned about the user through health care and what the user has done based on previous treatments using the device.

BRIEF DESCRIPTION OF THE DRAWINGS

The invention may be more readily understood by referring to the accompanying drawings in which:

FIG. 6 is a flow diagram showing a method of detecting force applied by the percussive massage device in accordance with a preferred embodiment;

FIG. 7 is a flow diagram showing a method of generating a lookup table correlating voltage to force in accordance with a preferred embodiment;

FIG. 13 is a flow diagram showing a method of detecting force applied by a percussive massage device in accordance with a preferred embodiment;

FIG. 14 is a flow diagram showing a method of generating a lookup table correlating power to force in accordance with a preferred embodiment;

FIG. 25 is a chart showing steps of Protocol 1 in accordance with a method of performing a routine for a percussive massage device;

FIG. 26 is a chart showing steps of a "Shin Splints" protocol in accordance with a method of performing a routine for a percussive massage device;

Like numerals refer to like parts throughout the several views of the drawings.

DETAILED DESCRIPTION OF THE PREFERRED EMBODIMENTS

Figure 1:
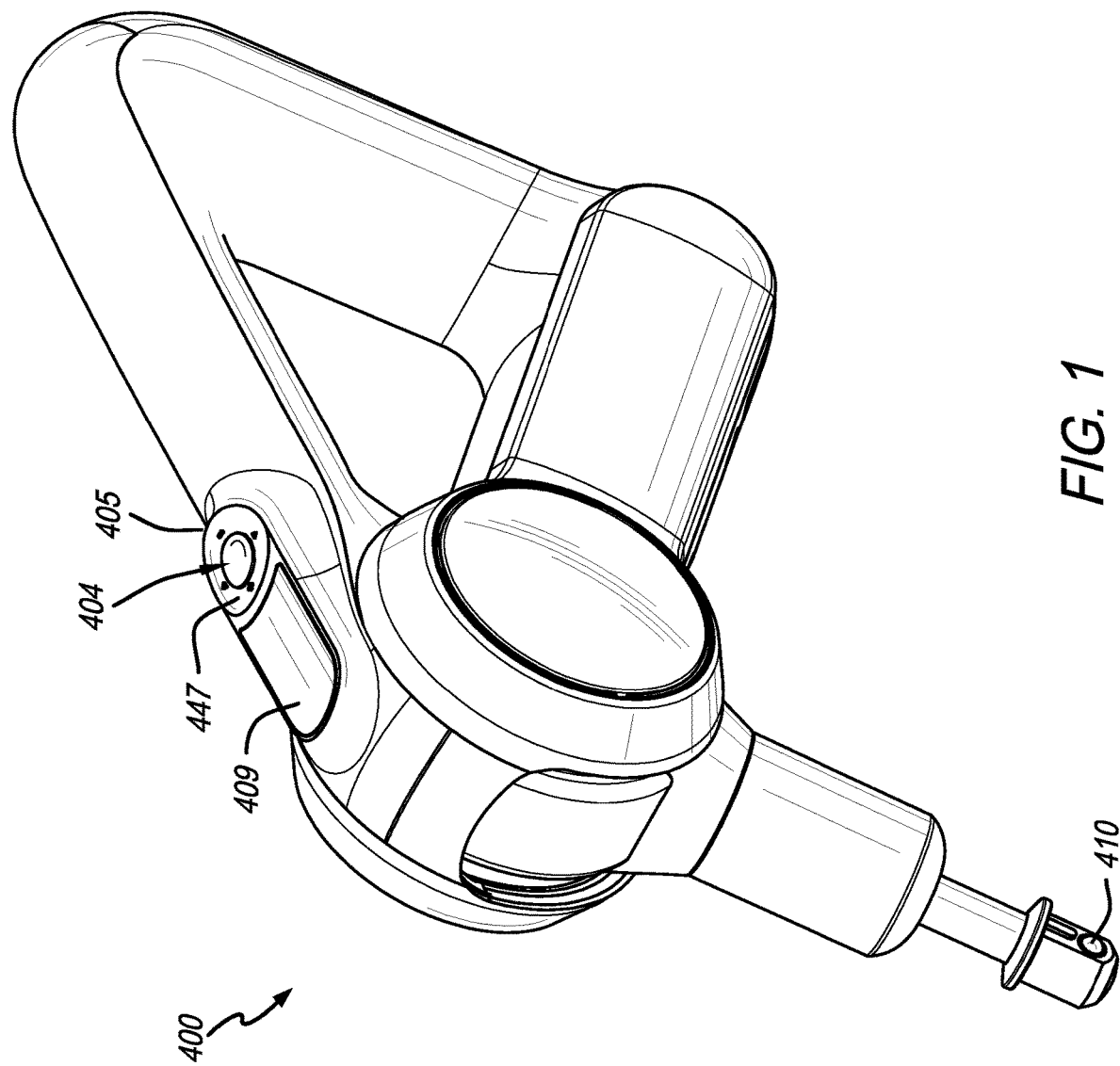
FIG. 1 is a drawing of an exemplary percussive massage device.

The following description and drawings are illustrative and are not to be construed as limiting. Numerous specific details are described to provide a thorough understanding of the disclosure. However, in certain instances, well-known or conventional details are not described in order to avoid obscuring the description. References to one or an embodiment in the present disclosure can be, but not necessarily are references to the same embodiment; and, such references mean at least one of the embodiments. If a component is not shown in a drawing then this provides support for a negative limitation in the claims stating that that component is "not" present. However, the above statement is not limiting and in another embodiment, the missing component can be included in a claimed embodiment.

Reference in this specification to "one embodiment," "an embodiment," "a preferred embodiment" or any other phrase mentioning the word "embodiment" means that a particular feature, structure, or characteristic described in connection with the embodiment is included in at least one embodiment of the-disclosure and also means that any particular feature, structure, or characteristic described in connection with one embodiment can be included in any embodiment or can be omitted or excluded from any embodiment. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others and may be omitted from any embodiment. Furthermore, any particular feature, structure, or characteristic described herein may be optional. Similarly, various requirements are described which may be requirements for some embodiments but not other embodiments. Where appropriate any of the features discussed herein in relation to one aspect or embodiment of the invention may be applied to another aspect or embodiment of the invention. Similarly, where appropriate any of the features discussed herein in relation to one aspect or embodiment of the invention may be optional with respect to and/or omitted from that aspect or embodiment of the invention or any other aspect or embodiment of the invention discussed or disclosed herein.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks: The use of highlighting has no influence on the scope and meaning of a term; the scope and meaning of a term is the same, in the same context, whether or not it is highlighted.

It will be appreciated that the same thing can be said in more than one way. Consequently, alternative language and synonyms may be used for any one or more of the terms discussed herein. No special significance is to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any exemplified term. Likewise, the disclosure is not limited to various embodiments given in this specification.

Without intent to further limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions, will control.

It will be appreciated that terms such as "front," "back," "top," "bottom," "side," "short," "long," "up," "down," "aft," "forward," "inboard," "outboard" and "below" used herein are merely for ease of description and refer to the orientation of the components as shown in the figures. It should be understood that any orientation of the components described herein is within the scope of the present invention.

Referring now to the drawings, which are for purposes of illustrating the present invention and not for purposes of limiting the same, the drawings show an intelligence engine system and method in accordance with preferred embodiments of the present invention. FIG. 1 is a drawing of an exemplary percussive massage device 400. Many of the components and characteristics of the percussive massage device 400 are the same or similar as those discussed in the applications incorporated by reference herein.

Figure 2:
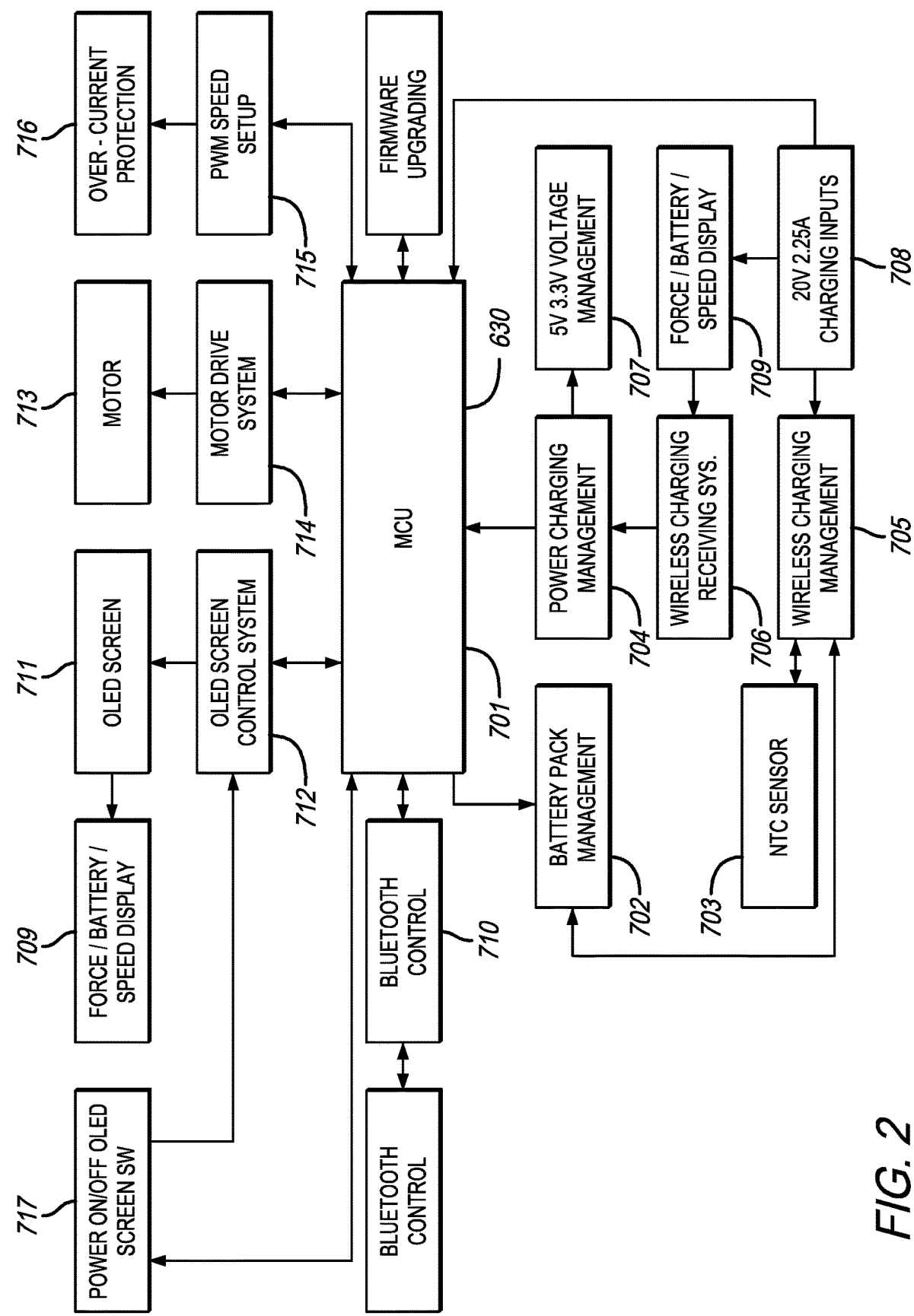
FIG. 2 is a block diagram showing interconnected components of a percussive massage device with a force meter.

As shown in FIGS. 2-29, embodiments in accordance with a percussion massage device with a force meter are shown. In particular, FIG. 2 is a block diagram showing interconnected components of a percussive therapy device with a force meter 400. In an embodiment, the percussive therapy device with force meter 400 includes a microcontroller unit 701, a battery pack management unit 702, an NTC sensor 703, a power charging management unit 704, a wireless charging management unit 705, a wireless charging receiving system 706, a voltage management unit 707 (5V 3.3V Voltage Management in drawings), battery charging inputs 708 (20V 2.25 A Charging Inputs in drawings), a display 709 (Force/Battery/Speed Display in drawings), a wireless control unit 710 (Bluetooth Control in drawings), an OLED screen 711, an OLED screen control system 712, a motor 713, a motor drive system 714, a PWM speed setup unit 715, an over-current protection unit 716, and a power switch unit 717 (Power On/Off OLED Screen SW in drawings). In the embodiment shown in accordance with FIG. 2, each block in the diagram is shown as a separate component. In alternative embodiments, however, certain components may be combined without departing from the scope of the present disclosure.

The microcontroller unit 701, in an embodiment, is a microcontroller unit including a processor, a memory, and input/output peripherals. In other embodiments, however the microcontroller unit 701 is an ST Microelectronics STM32F030K6 series of microcontroller units, STM32F030C8T6 series of microcontrollers, STM32F030CCT6 series of microcontrollers, or an equivalent microcontroller.

One of ordinary skill would understand that the memory of the microcontroller unit 701 is configured to store machine-readable code for processing by the processor of the microcontroller unit 701. Various other configurations may exist depending on whether the designer of the percussive massage device with force meter 400 desires to implement the machine-readable code in software, firmware, or both. In an embodiment, the machine-readable code is stored on the memory and configured to be executed by a processor of the microcontroller 701. In an embodiment, the machine-readable code is stored on computer-readable media.

The battery pack management unit 702, in an embodiment, is implemented in firmware or software and configured to be used in connection with the microcontroller unit 701. In this embodiment, the firmware or software is stored in memory (not shown) and configured to be obtainable by the microcontroller unit 701. The battery pack management unit 702 may also be a combination of firmware, software, and hardware, in another embodiment. The battery pack management unit 702 is coupled with the NTC sensor 703. The NTC sensor 703 is a negative temperature coefficient thermistor used by the battery pack management unit 702 to sense temperature of the battery pack. For example, the NTC sensor 703 is a thermistor with B value of 3950+/−1%, and a resistance of 10 kΩ. In another example, the thermistor has a resistance of 100 kΩ. One of ordinary skill in the art would recognize that a thermistor is a resistor whose resistance is dependent upon temperature. In other embodiments, however, the NTC sensor 703 may be another type of temperature sensing device or component used in connection with the battery pack management unit 702.

The power charging management unit 704, in an embodiment, is implemented in firmware or software and configured to be used in connection with the microcontroller unit 701. Similarly to the battery pack management unit 702, the power charging management unit 704 firmware or software is stored in memory (not shown) and configured to be obtainable by the microcontroller unit 701. The power charging management unit 704 may also be a combination of firmware, software, and hardware, in another embodiment. In various embodiments, the power charging management unit 704 is configured to charge a battery pack via a direct connection or through an external charger, such as when configured to be operable with rechargeable batteries.

The wireless charging management unit 705, in an embodiment, is coupled to the battery pack management unit 702 and the battery charging inputs 708. In other embodiments, the battery or battery pack is charged using other conventional methodologies, such as, for example, charging the battery or battery pack using a wire or cord coupled to the battery charging inputs 708.

The wireless charging receiving system 706, in an embodiment, is coupled to the power charging management unit 704 and the display 709. The wireless charging receiving system 706 includes one or more of firmware, software, and hardware. In an embodiment, the wireless charging receiving system 706 is configured to receive information pertaining to battery capacity, charging metrics, and other information pertaining to wireless charging, and to pass along the information to the power charging management unit 704. The wireless charging receiving system 706 preferably includes a wireless charging pad used to charge the percussive massage device with force meter 400. One of ordinary skill in the art would understand that a variety of wireless charging devices may be utilized to wirelessly charge the percussive massage device with force meter 400. As one example, the Qi wireless charging standard and related devices may be utilized to wirelessly charge the percussive massage device with force meter 400.

The voltage management unit 707, in an embodiment, is a DC voltage regulator that steps down 5 volt to 3.3 volt power for use by the microcontroller unit 701. The voltage management unit 707 may also perform additional functions for management of 3.3 volt power for use by the microcontroller unit 701. In an embodiment, the voltage management unit 707 is implemented using a series of electronic components such as, for example, implementing a resistive divider using electronic components. In another embodiment, the voltage management unit 707 is a stand-alone voltage regulator module and/or device designed to step down voltage from 5 volts to 3.3 volts. One of ordinary skill in the art would understand the various methodologies and devices available to step down 5 volts to 3.3 volts.

The battery charging inputs 708, in an embodiment, are interfaces by which a wire or cord may be inserted for charging the percussive massage device with force meter 400. For example, a standardized barrel connector is the battery charging inputs 708. In another example, the battery charging inputs 708 is a USB connector. Other more specialized charging methodologies may require a particular battery charging input not described above.

The display 709, in an embodiment, displays a series of LEDs depicting an amount of force applied by the percussive massage device with force meter 400. In an alternative embodiment, the display 709 displays a series of LEDs depicting the current battery or battery pack charge of the percussive massage device with force meter 400. In yet another embodiment, the display 709 displays a series of LEDs depicting the current speed of the percussive massage device with force meter 400. One of ordinary skill in the art would recognize that while LEDs have been specified in the above-referenced embodiments, other embodiments not using LEDs are within the scope of this disclosure, such as, for example, liquid crystal displays, OLEDs, CRT displays, or plasma displays. One of ordinary skill in the art would also understand that it may be advantageous in an embodiment utilizing a battery or battery pack to use low-power options to ensure battery power longevity. In an embodiment, the display 709 is a 128×64 pixel OLED display.

The wireless control unit 710 is a wireless connectivity device that may be implemented in a wireless microcontroller unit. In an embodiment, the wireless control unit 710 is a Bluetooth transceiver module configured to couple, via Bluetooth, to a remote device. In an embodiment, the Bluetooth module is a Bluetooth Low-Energy (BLE) module configured to be run in broadcast mode. The wireless control unit 710 is coupled to the microcontroller unit 701. In an embodiment, the remote device is a smartphone having an embedded Bluetooth module. In an alternative embodiment, the remote device is a personal computer having Bluetooth connectivity. In other embodiments, other wireless connectivity standards besides the Bluetooth wireless standard may be utilized. It will be appreciated that the Bluetooth connectivity or other wireless connectivity may be described herein as being implemented in a wireless connection device. The wireless connection device can be a separate module, can be included in the MCU or other component of the device, or can be a separate chip. In summary, the percussive therapy device including a wireless connection device means that the percussive massage device can connect to another electronic device wirelessly (e.g., a phone, tablet, computer, computer, voice controlled speaker, regular speaker, etc.). One of ordinary skill in the art would recognize that low-power wireless control modules may be advantageous when the percussive massage device with force meter 400 is utilizing a battery or battery pack.

The OLED screen 711 and the OLED screen control system 712, in an embodiment, are configured to display substantially the same information as the display 709 referenced above. The OLED screen 711 is coupled to the OLED screen control system 511. The OLED screen control system 712 is coupled to the microcontroller unit 701, the OLED screen 711, and the power switch unit 717. In an embodiment, the display 709 and the OLED screen 711 may be redundant and it may only be necessary to utilize one or the other.

The motor 713, in an embodiment, is a brushless direct current (BLDC) motor. The motor 713 and the motor drive system 714, in an embodiment, are configured to vary the speed (i.e., rotational motion) that may be converted to reciprocal motion. In other embodiments, the motor 713 is a brushed DC motor, a brushed AC motor, or a brushless AC motor. One of ordinary skill in the art would understand that choosing a brushless or brushed motor, or direct current or alternating current, may vary depending on the application and intended size, battery power, and use.

The PWM speed setup unit 715, in an embodiment, is used to control pulse width modulation utilized to drive the motor 713. The PWM speed setup unit 715 is coupled to the microcontroller unit 701 and the over-current protection unit 716. One of ordinary skill in the art would understand that pulse width modulation is one way to vary the average power applied to the motor 713, resulting in varying speed as desired. In alternative embodiments, one of ordinary skill in the art would understand that there are a variety of methods to vary the speed of a brushless DC motor. For example, voltage to the motor 713 may be controlled in other non-PWM methods.

The over-current protection unit 716, in an embodiment, may be a feature of an integrated system-in-package to prevent damage caused by high currents to the motor. In other embodiments, the over-current protection unit 716 is implemented using a series of electronic components configured to protect the motor from excessively high current.

The power switch unit 717, in an embodiment, is configured to turn on and turn off the percussive massage device with force meter 400. The power switch unit 717 is coupled to the OLED screen control system 712 and the microcontroller unit 701. In an embodiment, the power switch unit 717 is the switch 405.

Figure 3:
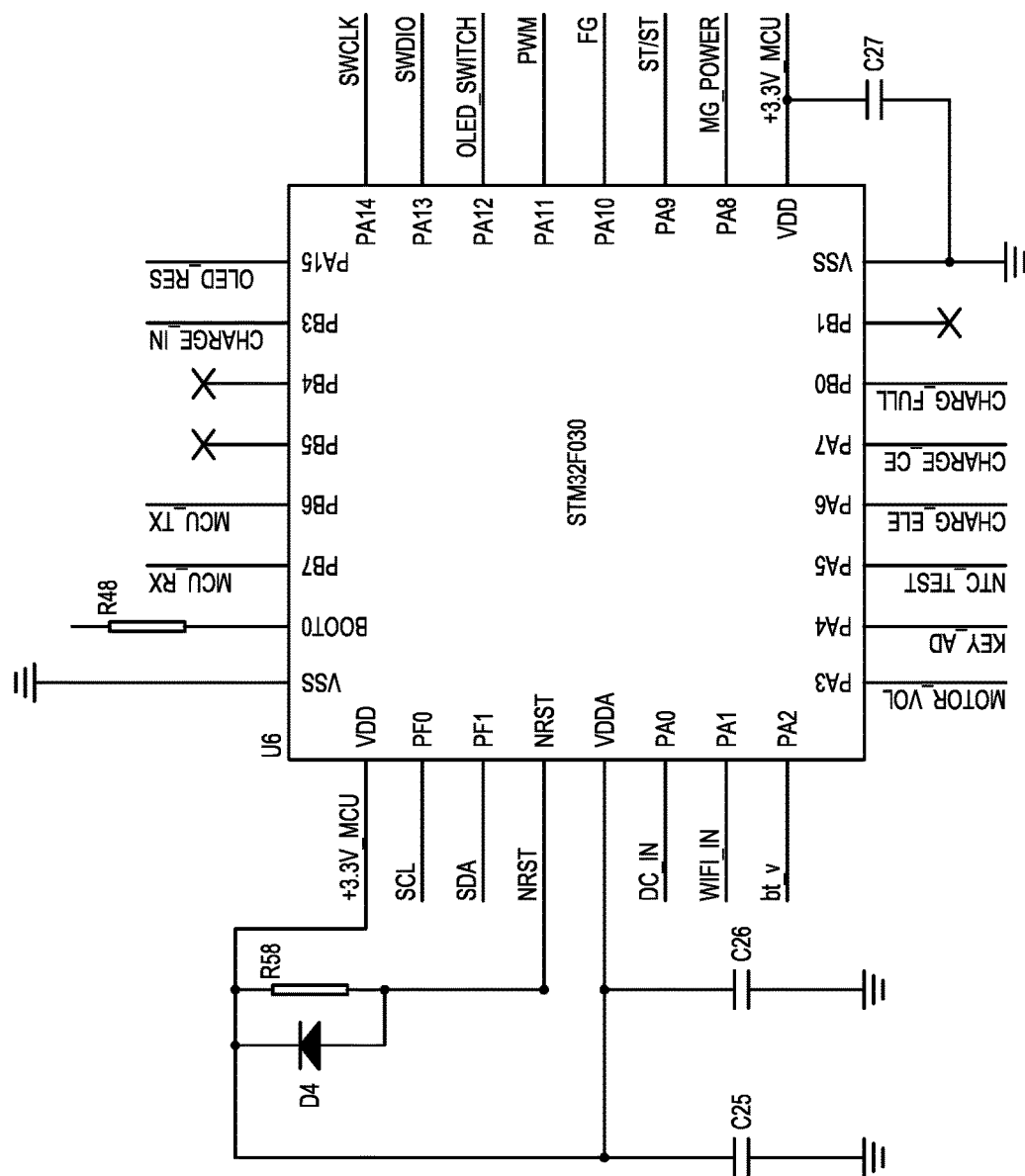
FIG. 3 is a circuit diagram of a microcontroller unit with pin outputs in accordance with one embodiment.

FIG. 3 shows a circuit diagram of the microcontroller unit 701 with pin outputs. In this embodiment, the STM32F030K6 series of microcontroller units is utilized. The circuit diagram depicts +3.3 volt power being provided to the VDD inputs of the microcontroller unit 701. Input PA3 is labeled "Motor_VOL", the voltage of the motor 713. Input PA2 is "bt_v", the battery or battery pack voltage. The microcontroller unit is configured to receive analog voltage on inputs PA2 and PA3 and to convert it to digital voltage using the microcontroller's analog-to-digital converter. In this embodiment, the analog-to-digital converter is a 12-bit ADC. One of ordinary skill in the art would understand that other microcontrollers may utilize voltage sensing and analog-to-digital converters to perform similar functions. In yet other embodiments, an analog-to-digital converter module separate from a microcontroller may be utilized.

Figure 4:
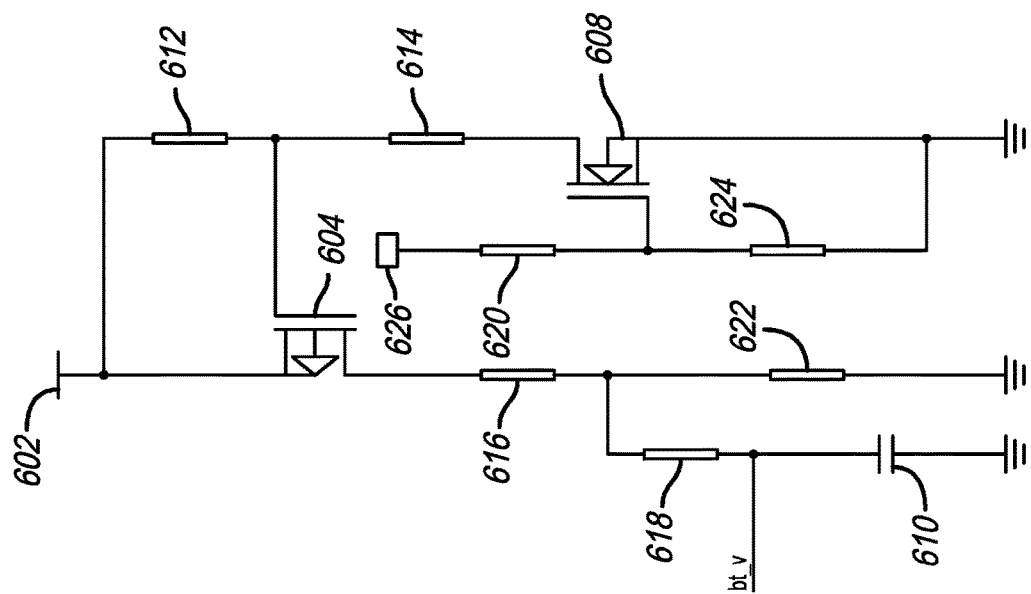
FIG. 4 is a circuit diagram used for battery voltage detection in accordance with one embodiment.

FIG. 4 shows a circuit diagram used for battery voltage detection. In this embodiment, +BT, the positive battery terminal 518, is coupled to a circuit consisting of a P-channel MOSFET 519, an N-Channel MOSFET 520, 0.1 μF capacitor 521, 100 kΩ resistors 522, 523, 68 kΩ resistor 524, 1 kΩ resistors 525, 526, and 10 kΩ resistors 527, 528. The circuit is configured to provide an input analog voltage of the battery or battery pack, or bt_v, to the microcontroller unit 701 of FIG. 3. In other embodiments, voltage of the battery or battery pack may be achieved using a voltage reader coupled to the terminals of the battery or battery pack.

Figure 5:
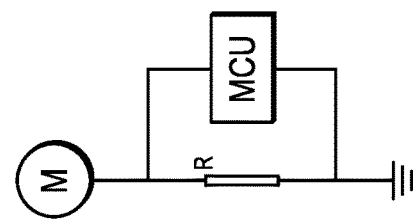
FIG. 5 is a circuit diagram for detection and measurement of voltage of the motor of the percussive massage device in accordance with one embodiment.

FIG. 5 shows a circuit diagram for detection and measurement of voltage of the motor 713 of the percussive massage device. In this embodiment, voltage sensing resistor 529 is coupled in parallel with the microcontroller unit 701, and coupled to the motor 713. In an embodiment, the voltage sensing resistor has a value of 0.0025 Ω. The circuit depicted in FIG. 5 is configured to provide the Motor_VOL input into the microcontroller unit 701 of FIG. 2. In an embodiment, the input analog voltage is amplified. In another embodiment, the voltage of the motor 713 is measured or sensed using a separate series of electronic components or a standalone device and input into a microprocessor for use with the method of displaying a force on the percussive massage device.

FIG. 6 is a flow diagram showing a method 800 of detecting force applied by the percussive massage device in accordance with a preferred embodiment. At Step 802, a voltage magnitude V is obtained. In an embodiment, voltage magnitude V is an analog voltage obtained by using the circuit disclosed in FIG. 2. In that circuit, a block curve signal from the motor 713 (i.e., a Hall effect sensor) is simulated in the circuit as current using the resistor R, which is placed in parallel with the microcontroller unit 701. In other embodiments, voltage that corresponds to the current operating speed of the motor 713 may be generated in a variety of other ways. The voltage magnitude V may be input to a microcontroller unit 701 that converts analog voltage to digital voltage using an analog-to-digital converter, such as that implemented in the STM32F030K6 microcontroller unit. The STM32F030K6 microcontroller unit coverts analog voltage magnitude to a digital code corresponding to the 12-bit ADC (i.e., 0 to 4096). The digital code represents a voltage magnitude corresponding to the original voltage magnitude V obtained.

At Step 804, a lookup table is generated that correlates voltage V to force magnitude F. In an embodiment, the lookup table is generated using a method 900 of generating a lookup table correlating voltage to force. For example, the force magnitude F may be expressed in pounds of force. In an alternative embodiment, the force magnitude F may be expressed in Newtons of force.

At Step 806, the force magnitude F corresponding to voltage magnitude V is displayed on the percussive massage device with force meter 400. In an embodiment, a series of LED lights may be utilized to depict varying amounts of force as the force is being applied by the percussive massage device with force meter 400. Thus, as the amount of force magnitude F increases, more LEDs on the series of LED lights will be lit. Preferably, the series of LED lights consists of 12 LED lights.

FIG. 7 is a flow diagram showing a method 900 of generating a lookup table correlating voltage to force. At Step 902, a maximum magnitude of force, $F_{MAX}$, is determined. The magnitude of $F_{MAX}$ may be determined by assessing the maximum desired force to apply using the percussive massage device with force meter 400. As an example, $F_{MAX}$ is 60 pounds of force.

At Step 904, a maximum magnitude of voltage, $V_{MAX}$, is determined. The magnitude of $V_{MAX}$ may be determined by assessing the maximum theoretical voltage change possible by the percussive massage device with force meter 400. As an example, $V_{MAX}$ is 1.8 volts.

At Step 906, $F_{MAX}$ is divided into equal increments. Using the above example from Step 902, 60 pounds of force is divided into 60 one-pound increments.

At Step 908, $V_{MAX}$ is divided into the same amount of increments as determined in Step 906 above. Thus, using the above example from Step 904, 1.8 volts is divided into 60 0.03-volt increments.

Figure 8:
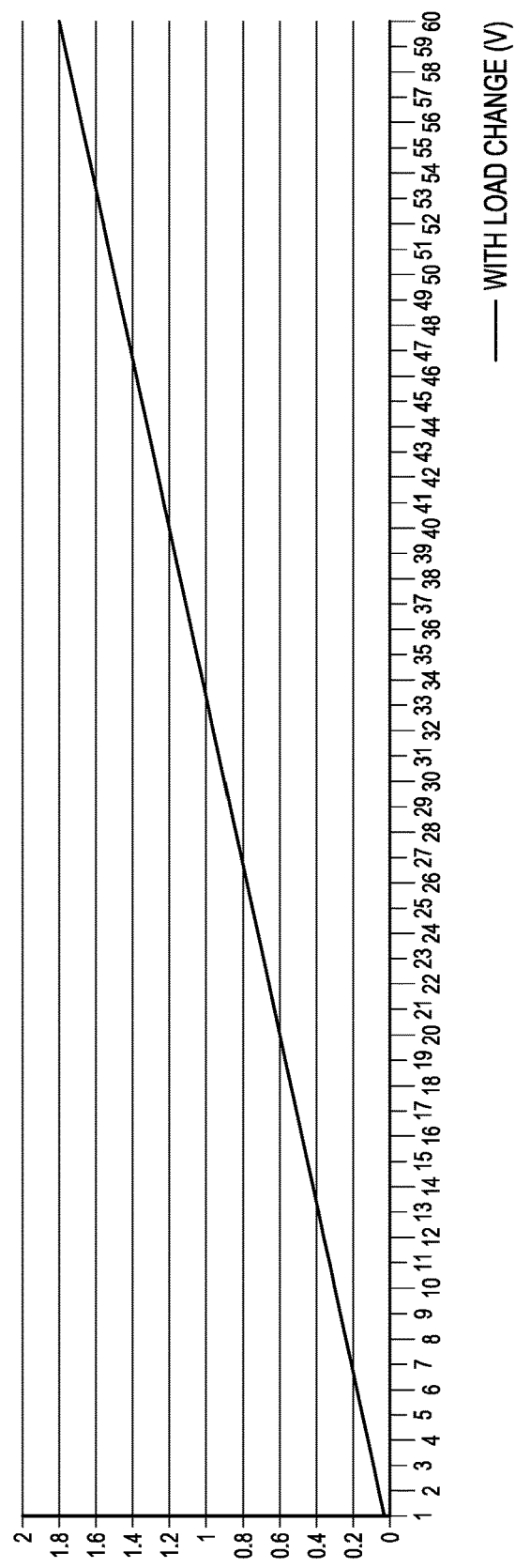
FIG. 8 is a graph plotting a lookup table for use by a method of detecting force applied by the percussive massage device that was generated by correlating voltage to force in accordance with a preferred embodiment.

At Step 910, a lookup table (LUT) is generated that correlates the increments of pounds of force with the increments of voltage. This necessarily creates a linear relationship between force and voltage. FIG. 8 is a graph plotting the LUT for use by the method of detecting force of FIG. 6 that was generated using the specific example identified in FIG. 7. The graph depicts calculated force that was calculated using the method 900.

A problem may arise in that the theoretical maximum voltage assumption at Step 904 in the method 900 is inaccurate. It may also be the case that as the percussive massage device with force meter 400 is used, the maximum available voltage degrades over time. In other words, the battery or battery pack voltage may decrease.

Figure 9:
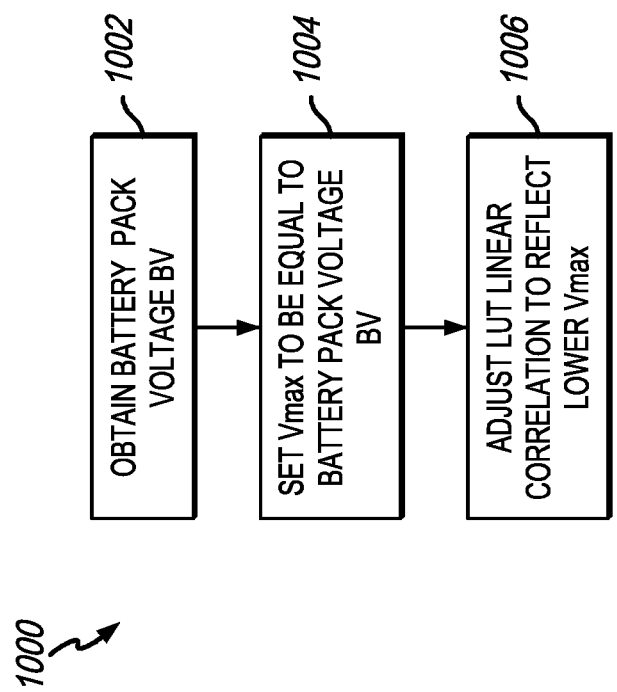
FIG. 9 is a flow diagram showing a method of calibrating a lookup table according to a preferred embodiment.

Accordingly, a method 1000 of calibrating the LUT generated by method 900 may be advantageous. FIG. 9 is a flow diagram showing a method 1000 of calibrating a LUT. At Step 1002, battery pack voltage BV is obtained. In an embodiment, battery pack voltage magnitude BV is an analog voltage obtained by using the circuit disclosed in FIG. 4. In that circuit, the battery pack voltage magnitude BV may be input to a microcontroller unit 701 that converts analog voltage to digital voltage using an analog-to-digital converter, such as that implemented in the STM32F030K6 microcontroller unit. The STM32F030K6 microcontroller unit coverts analog voltage magnitude to a digital code corresponding to the 12-bit ADC (i.e., 0 to 4096). The digital code represents a voltage magnitude corresponding to the original battery pack voltage magnitude BV obtained.

Figure 10:
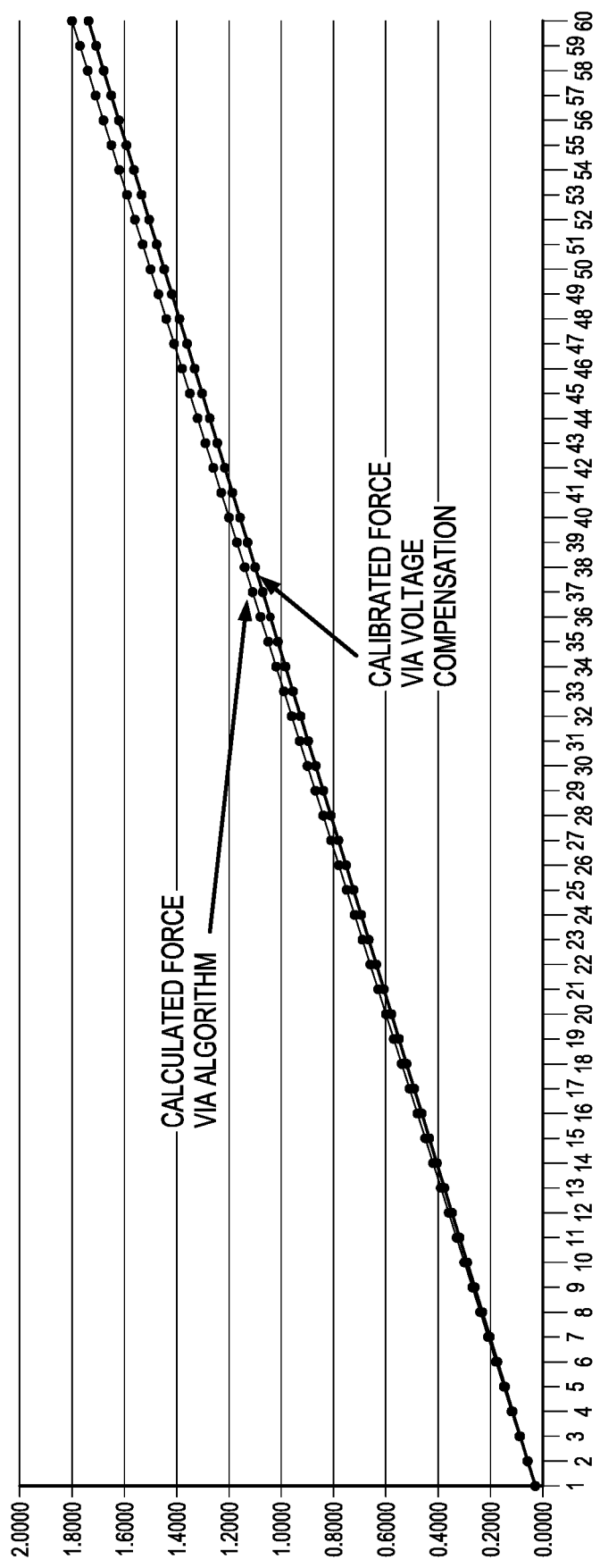
FIG. 10 is a graph plotting a lookup table generated by a method of detecting force applied by the percussive massage device against a lookup table calibrated by using a method of calibrating a lookup table according to a preferred embodiment.

At Step 1004, $V_{MAX}$ is set to the actual battery voltage magnitude BV output. As an example, may decrease from 1.8 volts to 1.74 volts, a 0.6 volt decrease. At Step 1006, the LUT linear correlation is adjusted to reflect the lower $V_{MAX}$. FIG. 10 is a graph plotting the LUT calculated by the method 900 against the LUT calibrated by using the method 1000.

The LUT resulting from method 1000 depicts a calibrated force rather than a calculated force.

Figure 11:
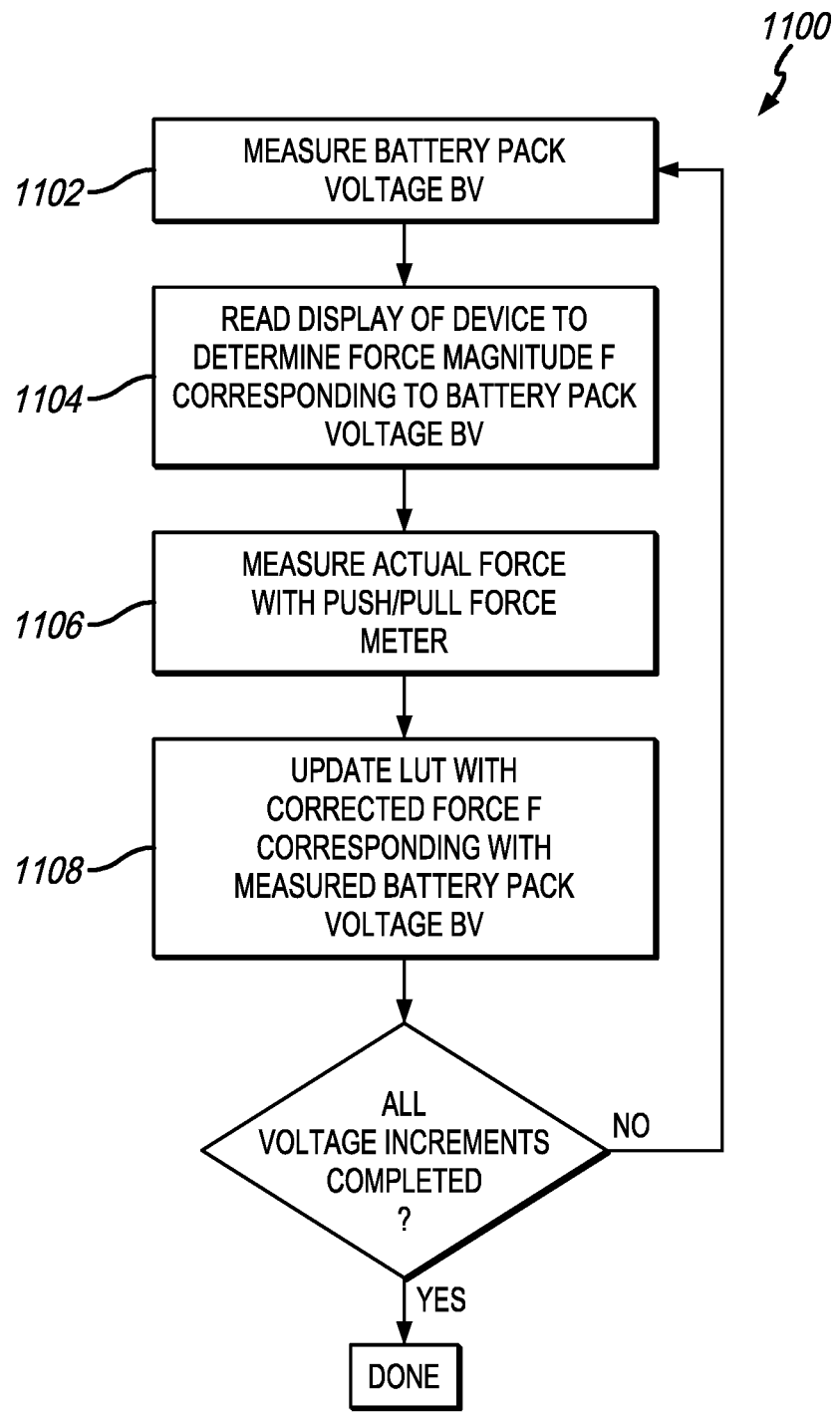
FIG. 11 is a flow diagram showing a method of calibrating a lookup table.

FIG. 11 is a flow diagram showing a method 1100 of calibrating a LUT. The method 1100 may be performed after the method 900, or entirely separately from the method 900. At Step 1102, battery pack voltage BV is measured. In an embodiment, the measurement is done without applying any force from the percussive massage device with force meter 400. In an embodiment, the battery pack voltage BV is measured using an external voltage meter. In another embodiment, the battery pack and/or microcontroller unit 701 have embedded solutions for directly measuring battery pack voltage BV.

At Step 1104, the display on the percussive massage device with force meter 400 that displays the force magnitude F is read to determine the force magnitude F corresponding to the measured battery pack voltage BV.

Figure 12:
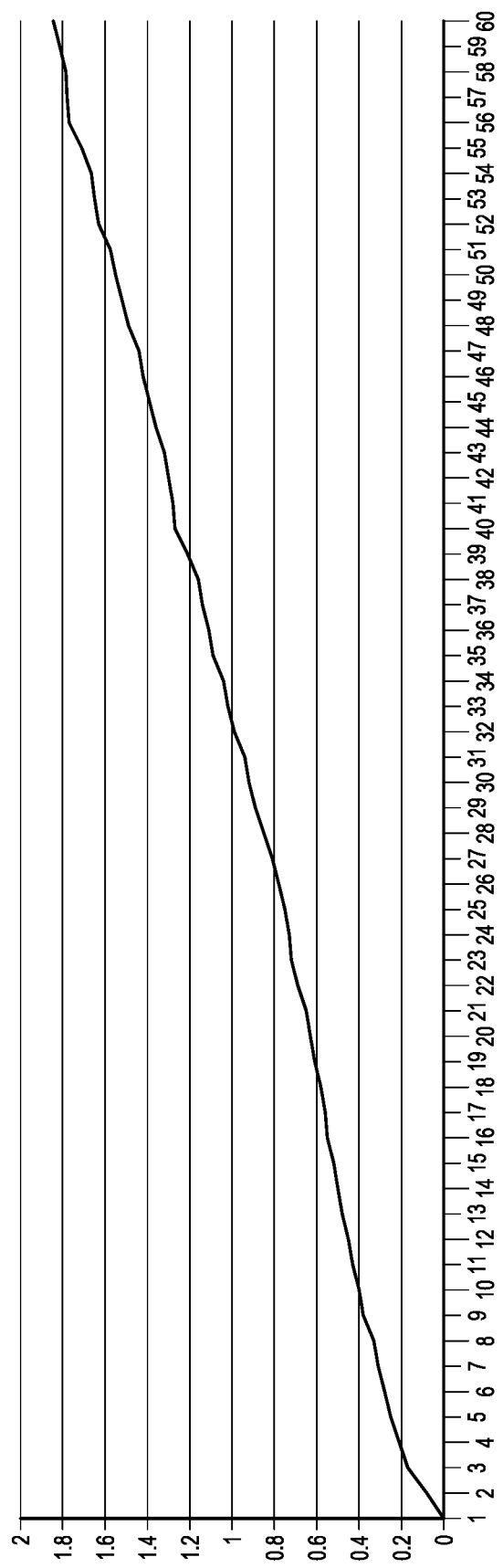
FIG. 12 is a graph plotting a lookup table after being calibrated in accordance with a preferred embodiment.

At Step 1106, a force meter is used to measure actual force being applied. In an embodiment, the force meter is a push/pull force meter. The direct measurement of force allows calibration of the LUT by comparing the displayed force magnitude F with the measured actual force. At Step 1108, the LUT is updated with a corrected force corresponding with the measured battery pack voltage BV. After Step 1108, Steps 1102-1106 are repeated for each successive voltage increment. In the embodiment depicted in accordance with the method 900, Steps 1102-1106 are repeated for every 0.03-volt increment. FIG. 12 is a graph plotting the LUT calculated by the method 1100 after all 3-volt increments had been updated.

FIG. 13 is a flow diagram showing a method 1200 of detecting force applied by a percussive massage device in accordance with a preferred embodiment. At Step 1202, current magnitude C of a battery pack is obtained. In an embodiment, current magnitude C is input into the microcontroller unit 701. At Step 1204, voltage magnitude BV of a battery pack is obtained. In an embodiment, voltage magnitude BV is input into the microcontroller unit 701. At Step 1206, power is calculated using the product of C and BV. In an embodiment, the microcontroller unit 701 is configured to calculate power by multiplying C and BV. At Step 1208, a lookup table is generated that correlates power magnitude P to force magnitude F. In an embodiment, the lookup table is generated using a method 1300 of generating a lookup table correlating power to force. For example, the power magnitude P may be expressed in watts. In an alternative embodiment, force magnitude F may be expressed in pounds of force or Newtons of force.

At Step 1210, the force magnitude F corresponding to power magnitude P is displayed on the percussive massage device with force meter 400. In an embodiment, a series of LED lights may be utilized to depict varying amounts of force as the force is being applied by the percussive massage device with force meter 400. Thus, as the amount of force magnitude F increases, more LEDs on the series of LED lights will be lit. Preferably, the series of LED lights consists of 12 LED lights.

FIG. 14 is a flow diagram showing a method 1300 of generating a lookup table correlating power to force. At Step 1302, a maximum magnitude of power, $F_{MAX}$, is determined. A theoretical maximum magnitude of power, however, is not a reasonable assumption if the total effective power may be calculated. Equation 1 may be utilized to determine Total Maximum Effective Power ($EP_{MAX}$).

$$\text{Total } EP_{MAX} = P_{MAX} \times \text{Total } EP \qquad \text{Equation 1:}$$

Equation 2 may be utilized to calculate Total EP, which is then input into Equation 1 above.

$$\text{Total } EP = EP_{BATTERY} \times EP_{PCBA} \times EP_{MOTOR} \qquad \text{Equation 2:}$$

where Total EP, $EP_{BATTERY}$, $EP_{PCBA}$, and $EP_{MOTOR}$ are all expressed in percentages, and where PCBA is a printed circuit board assembly.

In an embodiment, EP (Battery) is 85%, EP (PCBA) is 95%, and EP (Motor) is 75%. Thus, using Equation 2, Total EP is 85%*95%*75%=60.5625%.

In this embodiment, $P_{MAX}$ is calculated by multiplying the maximum voltage $V_{MAX}$ and the maximum amperage $C_{MAX}$ of the battery pack such as in Equation 3. $P_{MAX}$ is then input into Equation 1.

$$P_{MAX} = V_{MAX} \times C_{MAX}$$

In this embodiment, $V_{MAX}$ is 16.8 volts and $C_{MAX}$ is 20 amperes. Thus, $P_{MAX}$ is 336 watts.

Turning back now to Equation 1, if $P_{MAX}$ is 336 watts and Total EP is 60.5625%, then Total $EP_{MAX}$ is 203 watts.

At Step 1304, a minimum amount of power $P_{MIN}$, is determined. It will be recognized by one of ordinary skill in the art that the power without any force being applied (i.e., no load) will be non-zero. Thus, $P_{MIN}$ of 12 watts is assumed. One of ordinary skill will also understand that the value of is equivalent to the rated power without load, which may be derived from $V_{MAX}$ and $C_{MIN}$.

At Step 1306, a maximum magnitude of force, $F_{MAX}$, is determined. The magnitude of $F_{MAX}$ may be determined by assessing the maximum desired force to apply using the percussive massage device with force meter 400. As an example, $F_{MAX}$ is 60 pounds of force.

At Step 1308, Total $EP_{MAX}$ is divided into equal increments. In an embodiment, Total $EP_{MAX}$ is divided in 3 watt increments per one pound of force, starting at $P_{MIN}$ (12 watts). It will be recognized by one of ordinary skill in the art that if $F_{MAX}$ is 60 pounds of force, the total desired force output of the percussive massage device with force meter 400, then 60 pounds of force correlates to 189 watts, within the calculated Total $EP_{MAX}$.

Figure 15:
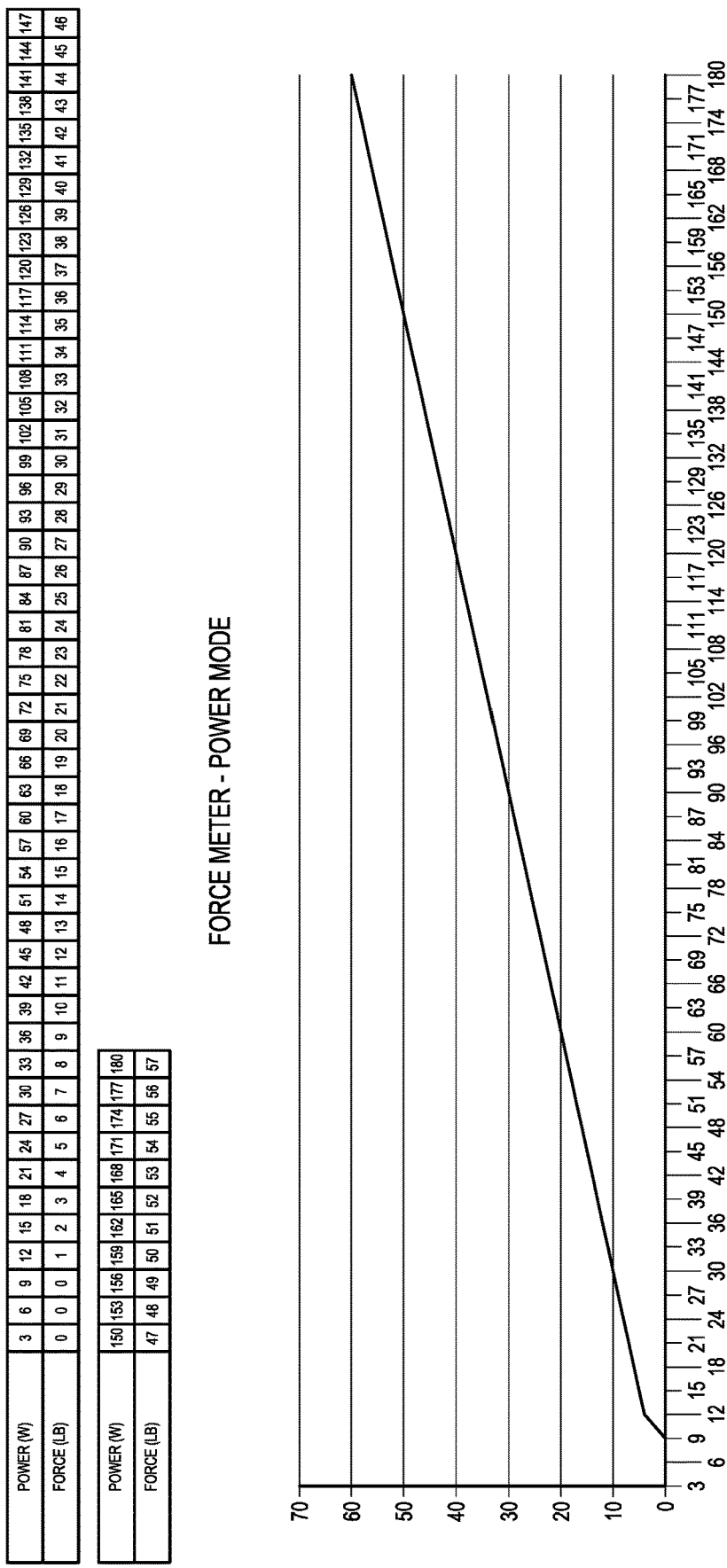
FIG. 15 is a graph plotting a lookup table for use by a method of detecting force of that was generated by correlating power to force in accordance with a preferred embodiment.

At Step 1310, a LUT is generated that correlates the increments of pounds of force with the increments of power in watts. This necessarily creates a linear relationship between force and voltage. FIG. 15 is a graph plotting the LUT for use by the method of detecting force of FIG. 13 that was generated using the specific example identified in FIG. 14. The graph depicts calculated force that was calculated using the method 1200.

Similarly to the method 900, a problem may arise in that the measured voltage of the battery pack at Step 1204 in the method 1200 is inaccurate. It may also be the case that as the percussive massage device with force meter 400 is used, the maximum available voltage degrades over time. In other words, the battery or battery pack voltage may decrease.

Figure 16:
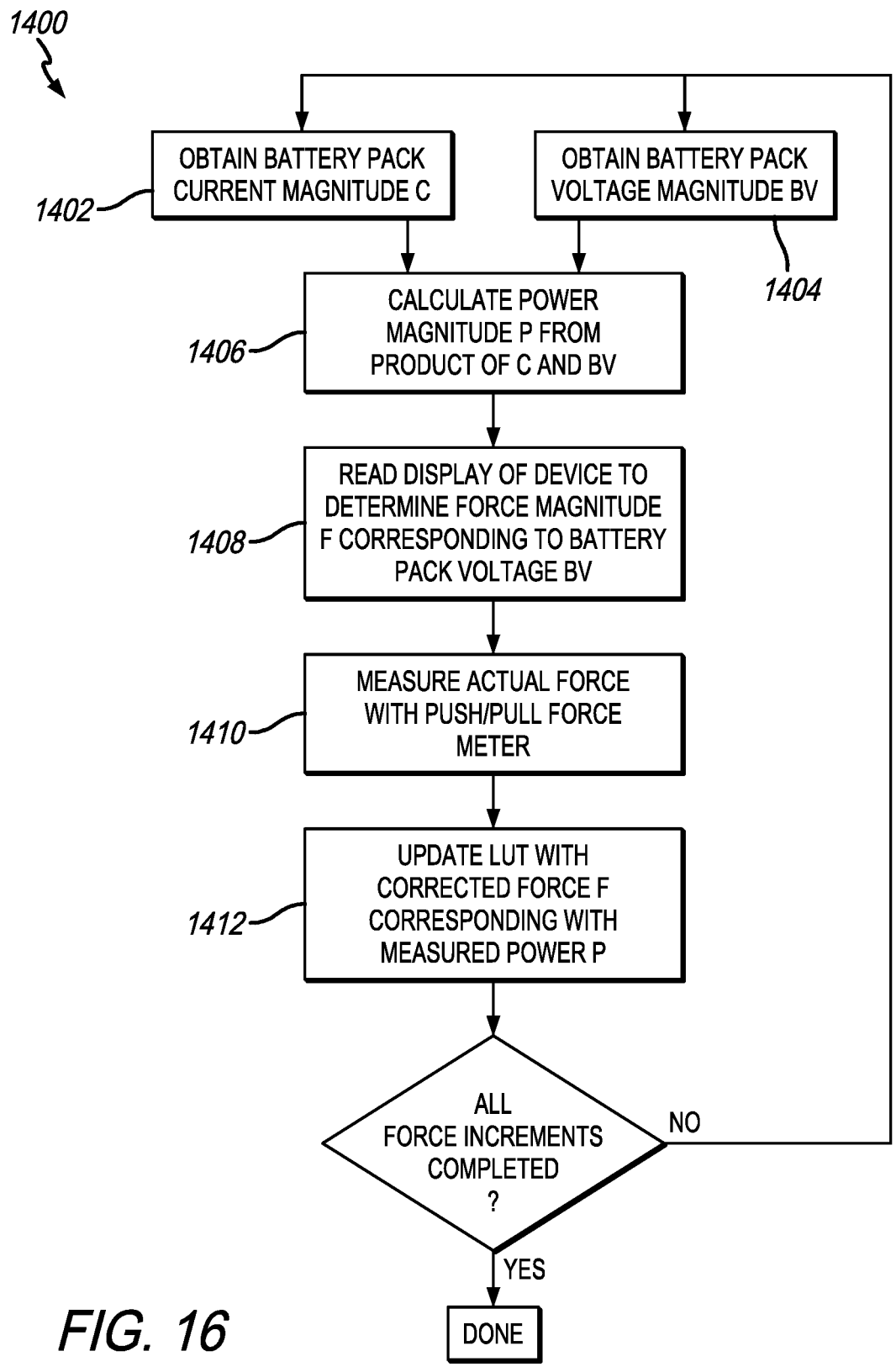
FIG. 16 is a flow diagram showing a method of calibrating a lookup table in accordance with a preferred embodiment.

FIG. 16 is a flow diagram showing a method 1400 of calibrating a LUT. The method 1400 may be performed after the method 900 or the method 1200, or entirely separately from the method 900 or the method 1200. At Step 1402, current magnitude C of a battery pack is obtained. In an embodiment, current magnitude C is input into the microcontroller unit 701.

At Step 1404, battery pack voltage BV is measured. In an embodiment, the measurement is done without applying any force from the percussive massage device with force meter 400. In an embodiment, the battery pack voltage BV is measured using an external voltage meter. In another embodiment, the battery pack and/or microcontroller unit

701 have embedded solutions for directly measuring battery pack voltage BV. At Step 1406, power is calculated using the product of C and BV. In an embodiment, the microcontroller unit 701 is configured to calculate power by multiplying C and BV.

Figure 17:
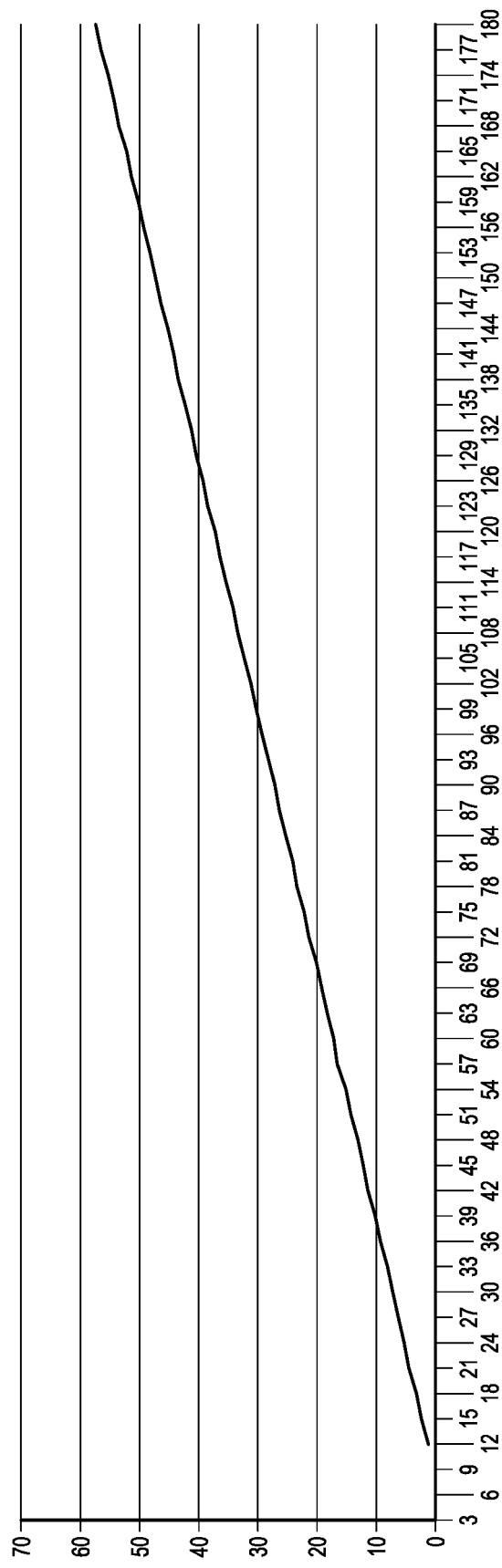
FIG. 17 is a graph plotting a lookup table after being calibrated in accordance with a preferred embodiment.

At Step 1408, the display on the percussive massage device with force meter 400 that displays the force magnitude F is read to determine the force magnitude F corresponding to the calculated power. At Step 1410, a force meter is used to measure actual force being applied. In an embodiment, the force meter is a push/pull force meter. The direct measurement of force allows calibration of the LUT by comparing the displayed force magnitude F with the measured actual force. At Step 1412, the LUT is updated with a corrected force corresponding with the measured power. After Step 1412, Steps 1402-1410 are repeated for each power or force increment. In the embodiment depicted in accordance with the method 900, Steps 1402-1410 are repeated for every 3-watt increment. FIG. 17 is a graph plotting the LUT calculated by the method 1400 after all 3-watt increments had been updated.

Figure 18:
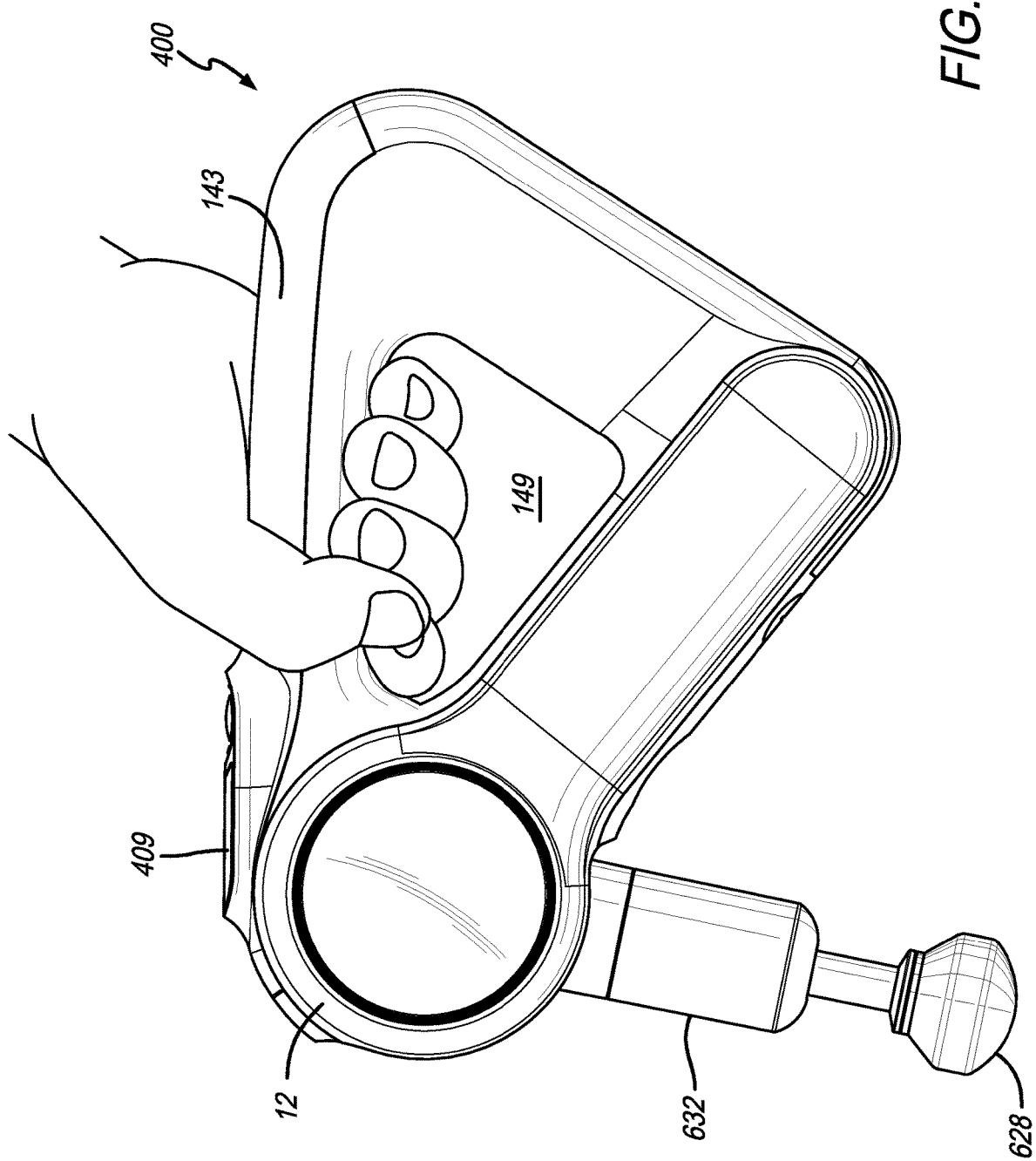
FIG. 18 is a side elevational view of the percussive massage device showing a user grasping the first handle portion.
Figure 19:
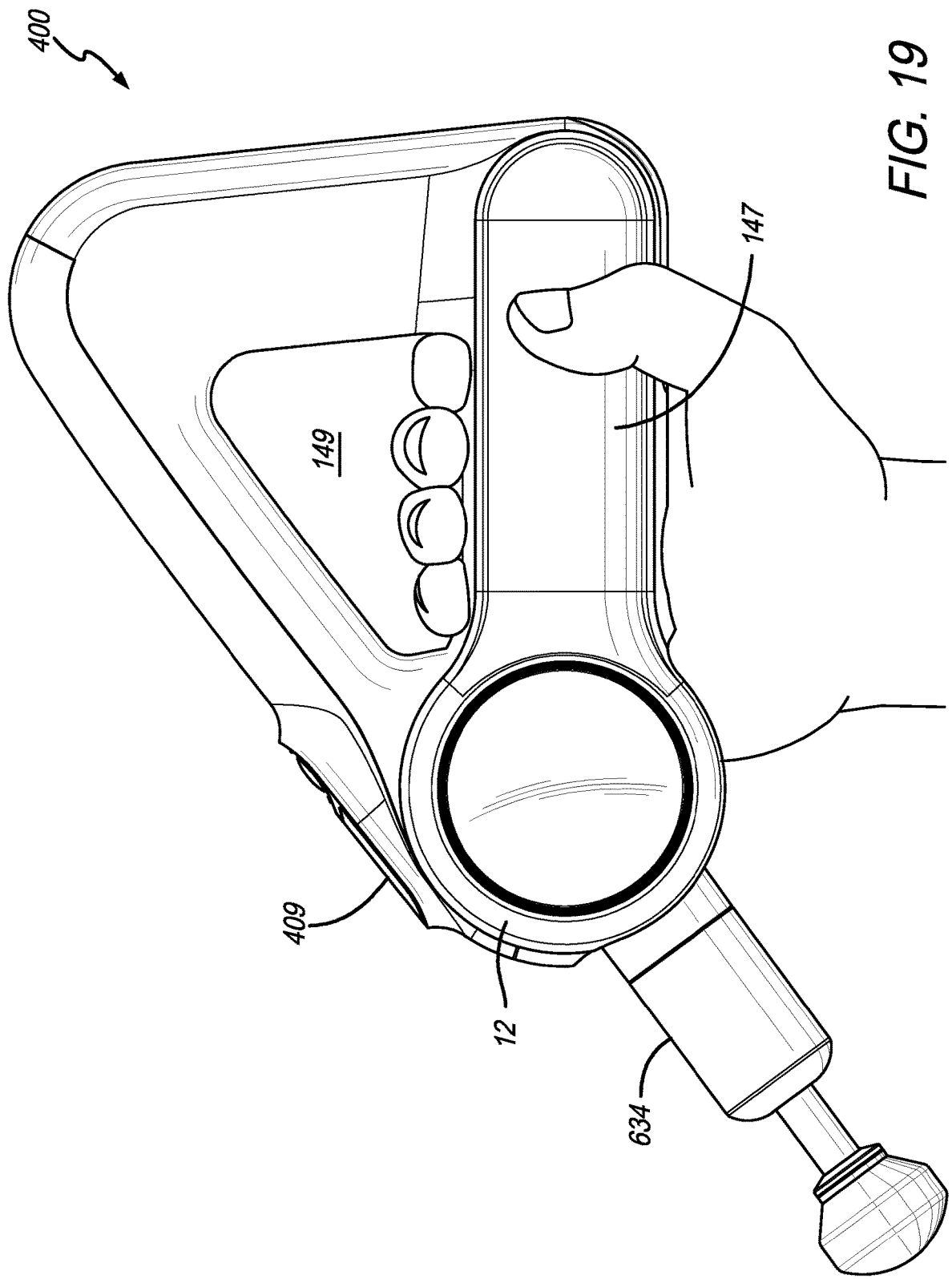
FIG. 19 is a side elevational view of the percussive massage device showing a user grasping the third handle portion.
Figure 20:
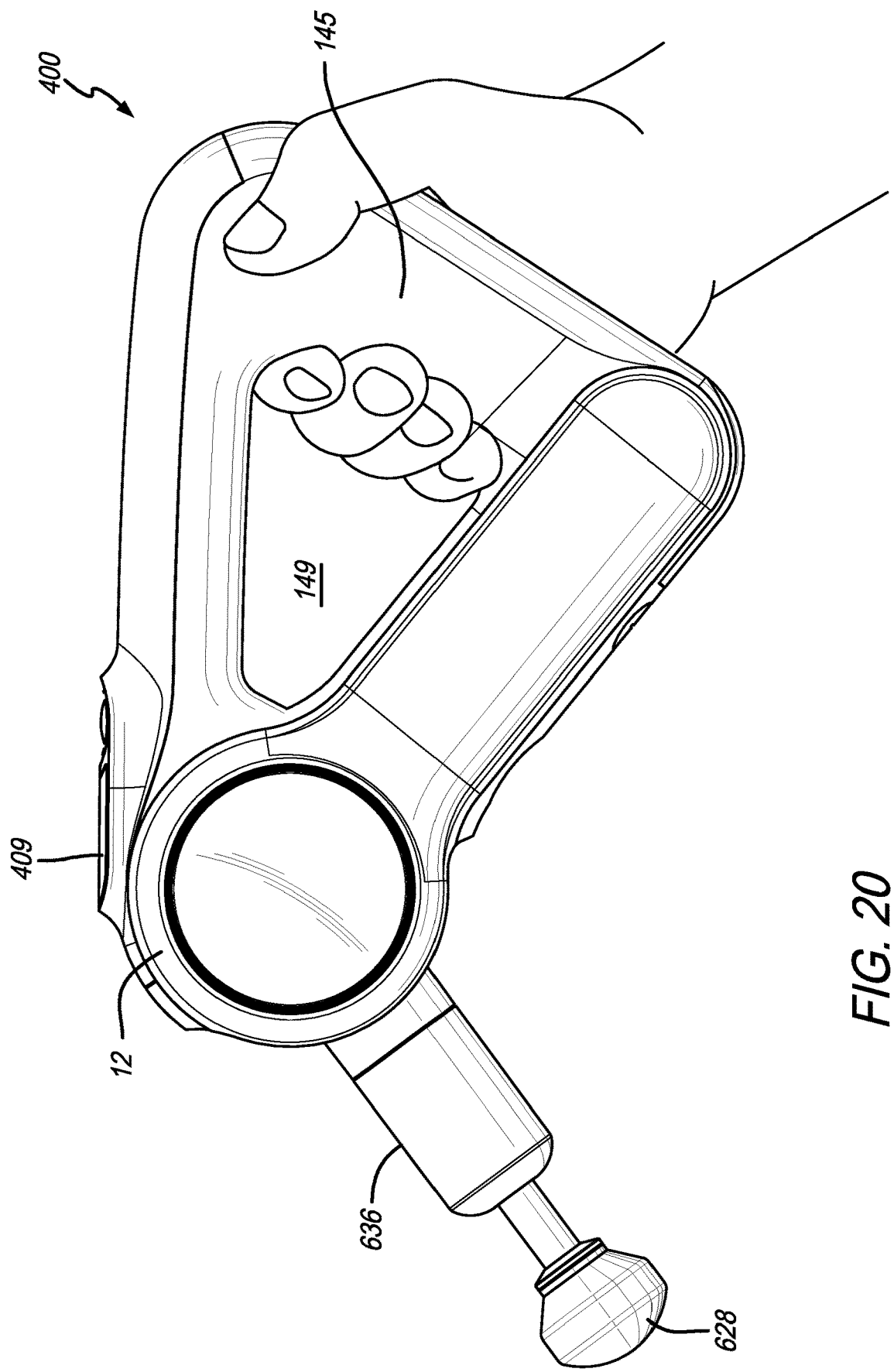
FIG. 20 is a side elevational view of the percussive massage device showing a user grasping the second handle portion.

FIGS. 18-24 show further views of percussive massage device 400. FIGS. 18-20 show that the percussive massage device 400 includes a triangle shape with first, second and third handle portions 143, 145 and 147 that cooperate to define the handle portion 149. All features and components described above with respect to any percussive therapy or massage devices may be included in the percussive massage device 400.

Figure 21:
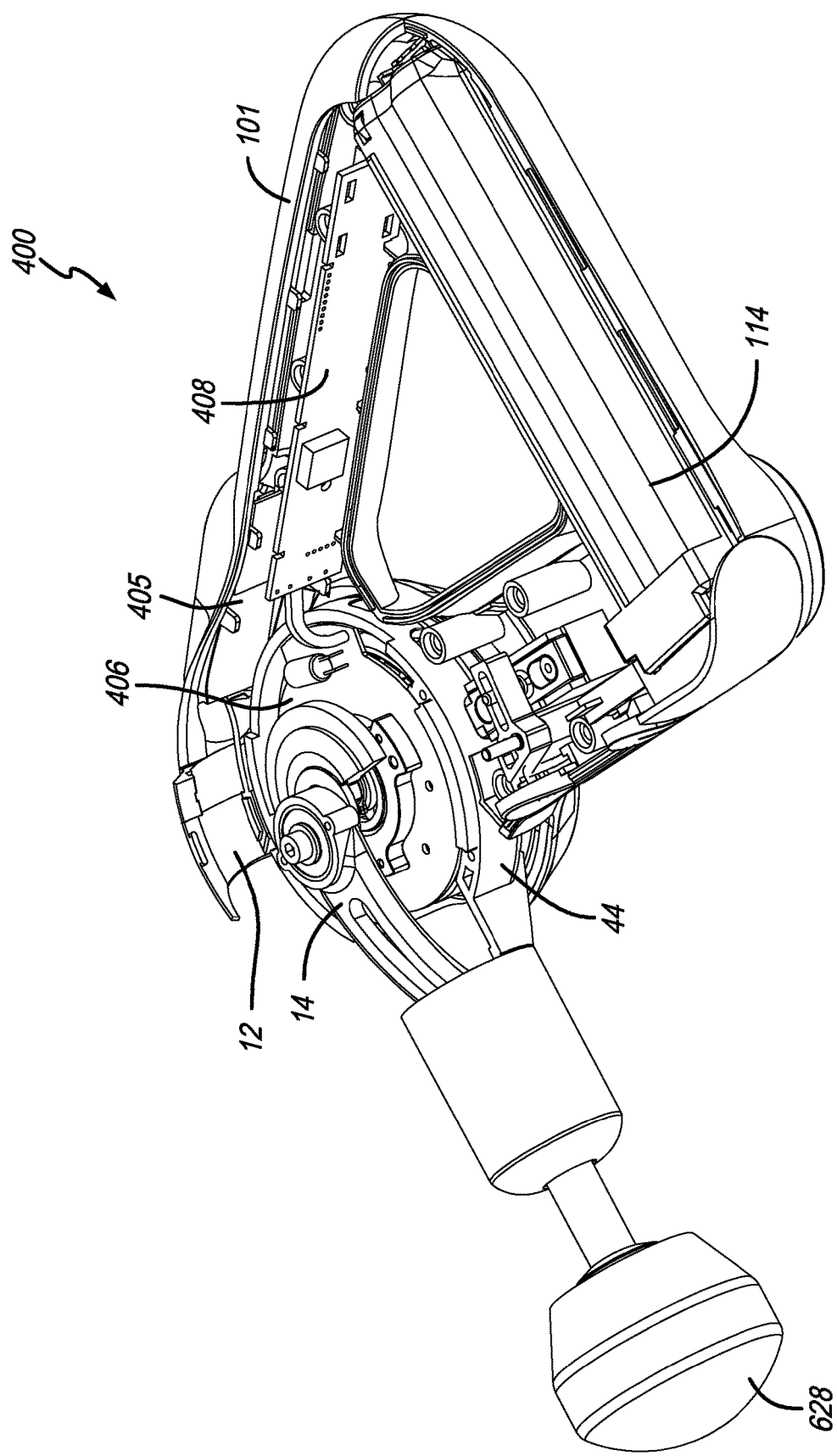
FIG. 21 is a perspective view of the percussive massage device of FIG. 18 with a portion of the housing removed.
Figure 22B:
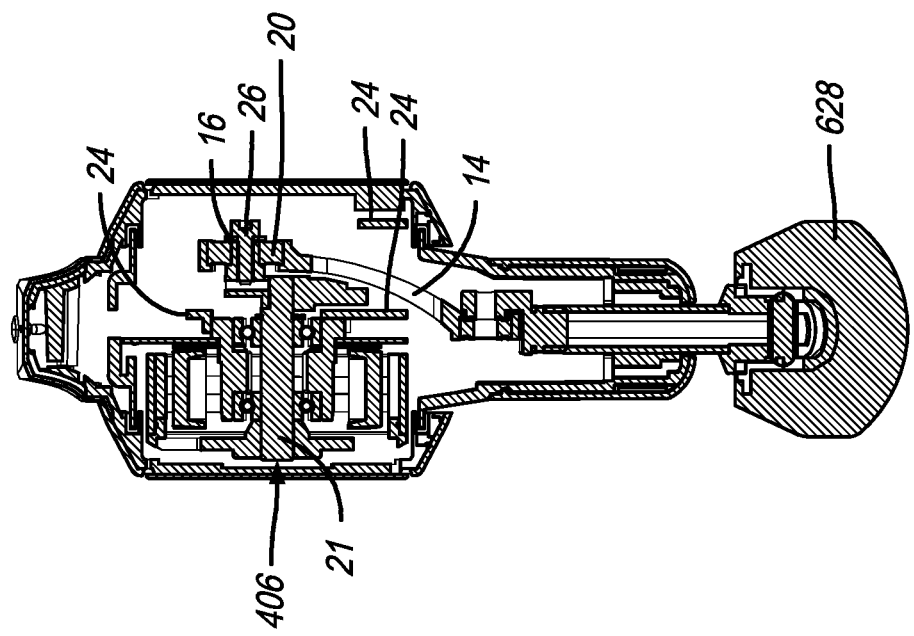
FIGS. 22A and 22B are cross sectional views of the head portion and motor.
Figure 22A:
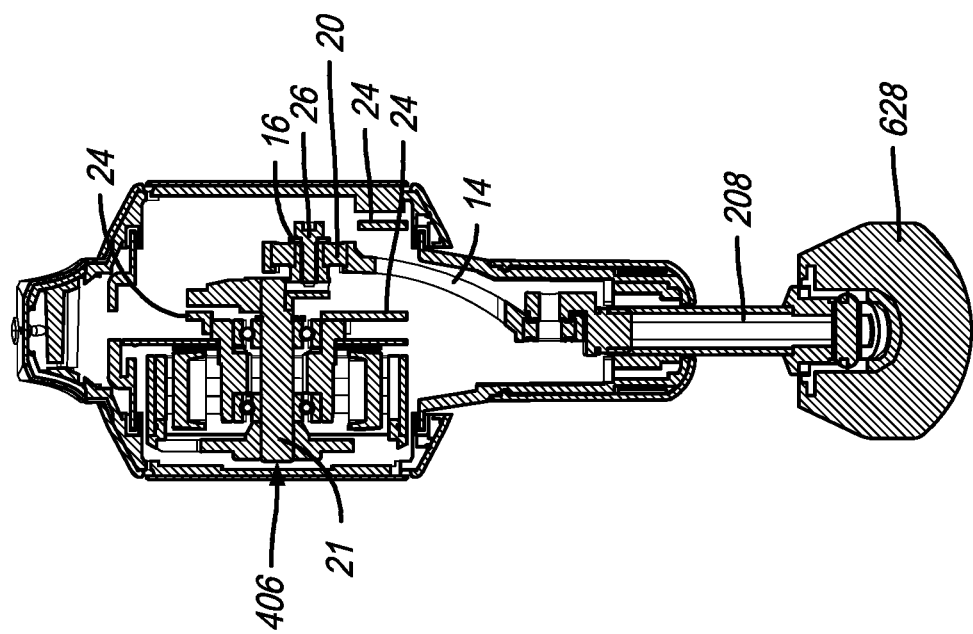
Figure 23:
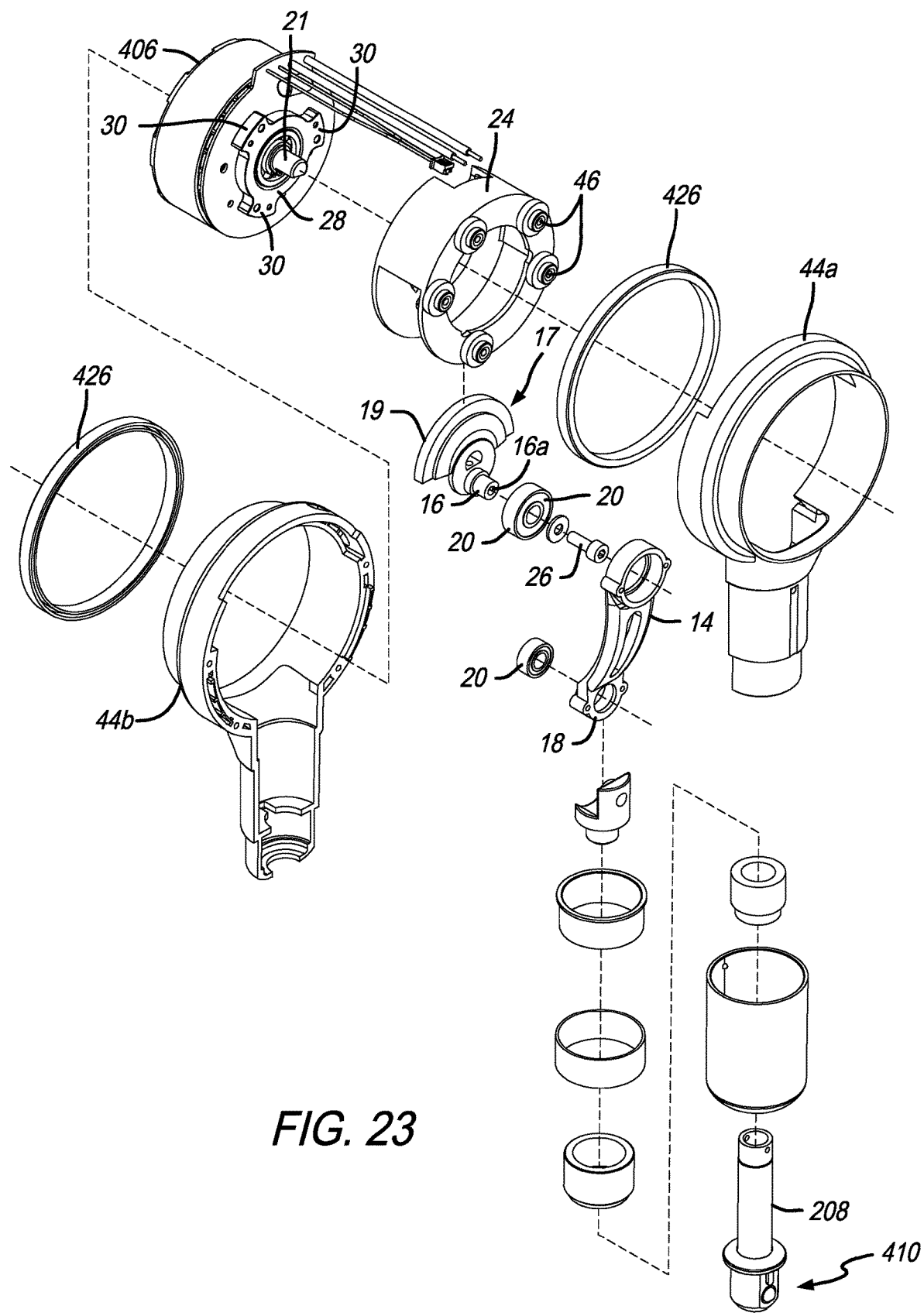
FIG. 23 is an exploded view of some of the internal components of a percussive massage device.

As shown in FIGS. 21-23, in a preferred embodiment, the brushless motor 406 is located in the head portion 12. The percussive massage device 400 can include a rotatable arm that is part of rotation housing 44 (shown in FIG. 21). The motor 406 is located in the rotation housing 44, which is housed with the head portion 12 of the housing 101. In another embodiment, the rotation capability can be omitted.

In a preferred embodiment, the device includes a push rod or shaft 14 that is connected directly to a shaft 16 that is rotated by the motor 406 and the motor shaft 21 extending therefrom. The shaft 16 can be part of a counterweight assembly 17 that includes a counterweight 19. In a preferred embodiment, the push rod 14 is L-shaped or includes an arc shape, as shown in FIGS. 22A-22B. Preferably, the point where the push rod 14 is connected to the shaft 16 is offset from the reciprocating path that the distal end 18 of the push rod 14 (and the massage attachment 628) travel. This capability is provided by the arc or L-shape. It should be appreciated that the push rod 14 is designed such that it can transmit the force at least partially diagonally or in an arc along its shape instead of vertically so the motor can be located at or near the middle of the device, otherwise a large protrusion would be necessary to keep the shaft in the center with the motor offset therefrom (and positioned in the protrusion). The arc also allows the push rod 14 to have a close clearance with the motor, as shown in FIGS. 22A and 22B and allows the outer housing to be smaller than similar prior art devices, therefore making the device 400 lower profile. FIG. 22A shows the push rod 14 at the bottom dead center of its travel and FIG. 22B shows the push rod 14 at the top dead center of its travel. Preferably one or more bearings 20 are included at the proximal end of the push rod 14 where it connects to the motor to counteract the diagonal forces and preventing the push rod 14 from moving and touching the motor 406. The bearing 20 is received on shaft 16 and a threaded fastener 26 is received in a co-axial opening 16a in shaft 16. The proximal end of the push rod 14 is received on bearing 20. These components are all shown in FIG. 23.

In another preferred embodiment, any of the devices taught herein can include the ability to vary the amplitude or stroke, thus providing a longer or shorter stroke depending on the application or needs of the user. For example, the stroke can change or be changed between about 8-16 mm. In another embodiment, the stroke can be varied up to 25 or more mm. The amplitude/stroke variability can also be part of the routines, presets or protocols discussed herein. For example, the device can include a mechanical switch that allows the eccentricity of the connector to be modified (e.g., between 4 mm and 8 mm). The mechanism can include a push button and a slider. The pin structure has a spring that lets it fall back into the locked position.

In a preferred embodiment, device 400 includes a number of dampening components that are made of an elastomer or the like and damp vibrations to keep the device relatively quiet. For example, as shown in FIG. 23, device 400 includes dampening rings 426 (similar to inner suspension rings 219) that surround the rotation housing 44 (with first and second rotation housing halves 44a and 44b) and help dampen the sound of vibration between the rotation housing and outer housing 101.

Figure 24:
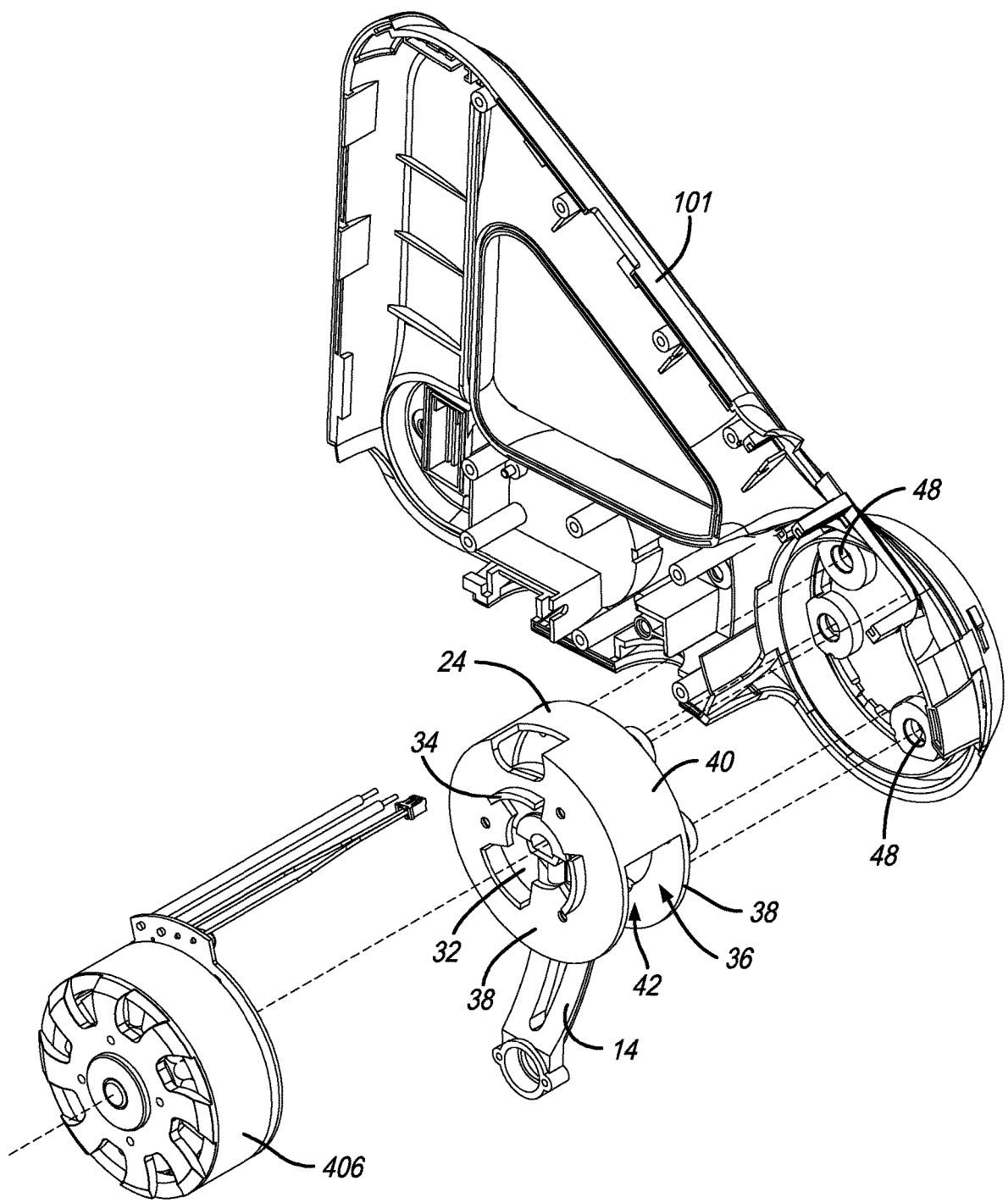
FIG. 24 is an exploded view of the motor and motor mount.

As shown in FIGS. 23 and 24, the device 400 preferably also includes a motor mount 24 that secures the motor 406 in place and is secured to the housing 101. Motor 406 includes a receiving member 28 with three protrusions 30 (and number between one and ten can be included) that is received in a protrusion opening 32 defined in the motor mount 24 (in first wall 38). Flanges 34 extending from the motor mount 24 help keep the protrusions 30 in place. The motor 406 is preferably secured via threaded fasteners or the like to the motor mount 24. Motor shaft 21 extends into the motor mount interior 36, which is defined between first and second walls 38 and a side 40 that extends part of the way around the circumference. The counterweight assembly 17, proximal end of the push rod 14 and related components for converting the rotation of the motor shaft 21 to reciprocating motion are position in the motor mount interior 36. The push rod 14 extends downwardly out of the motor mount interior and through a push rod opening 42 in the side 40. In a preferred embodiment, the motor mount 24 is connected directly to the housing 101 via fasteners 46 that are secured to mounting members 48 in the housing (see FIG. 24). It will be appreciated that the term push rod assembly used herein includes any of the components discussed herein or combinations thereof, e.g., push rod 14, output shaft 208, that extend from the rotating motor shaft 21, or the like that provide reciprocating motion and include the attachment on the distal end thereof. The push rod assembly also includes the male connector 410 (and any related components) or any other connector at the end of the reciprocating components that allows connection of an attachment to be used for massage or therapy.

In a preferred embodiment, the device 400 is associated with and can be operated by an app or software that runs on a mobile device such as a phone, watch or tablet (or any computer). The app can connect to the device 400 via Bluetooth or other wireless connection protocol. The app can have any or all of the following functions. Furthermore, any of the functions discussed herein can be added to the touch screen/scroll wheel or button(s) capability directly on the device. If the user walks or is located too far away from the device, the device will not work or activate. The device can be turned on an off using the app as well as the touch screen or button on the device. The app can control the variable speeds (e.g., anywhere between 1750-3000 RPM). A timer can be implemented so the device stops after a predetermined period of time.

In a preferred embodiment the device, via the app or the touch screen and other functional buttons, etc. includes different treatment protocols or routines associated therewith. During the routine, the device can vary different aspects or outputs of the device or make changes based on time, speed (frequency), amplitude (stroke), arm position, force, temperature, grip (i.e., which handle portion to grip), attachment (e.g., cone, ball, dampener, etc.) and body part. The device (via the app, touch screen, haptic feedback or audibly via a speaker) can also prompt the user to make some of these changes at certain points throughout the routine, e.g., arm position, grip, attachment changes and body part changes. One of ordinary skill in the art will understand that, depending upon the particular design of the device, one or more of these outputs are applicable, while in other devices, all options described are applicable.

When the start of the protocol is selected, the device runs through a preprogrammed routine. For example, the device may operate at a first RPM for a first period of time and then operate at a second RPM for a second period of time and/or at a first amplitude for a first period of time and then operate at a second amplitude for a second period of time. The routines can also include prompts (e.g., haptic feedback) for letting the user to know to move to a new body part. These routines or treatments can be related to recovery, blood flow increase, performance, etc. and can each include a preprogrammed routine or protocol. These routines can also help facilitate certain activities, such as sleep, interval training, stairs, post-run, post-workout, recovery, wellness, post-core exercise, high intensity (plyometric) workouts, among others. The routines can also assist in providing relief and recovery from ailments such as plantar fasciitis, "tech neck," muscle cramps, jet lag, sciatica, carpal tunnel, knots, and shin splints, among others. The routines can also prompt or instruct the user to switch attachments (e.g., attachment 628 shown in FIG. 20) or positions of the arm or rotation housing. The prompts can include sounds, haptic feedback (e.g., vibration of the device or mobile device), textual instructions or visual representation such as a graphic or picture on the app or touch screen, etc. For example, the app may instruct the user to start with the ball attachment with the arm in position two. Then the user hits start and the device runs at a first frequency for a predetermined amount of time. The app or device then prompts the user to begin the next step in the routine and instructs the user to change to the cone attachment and to place the arm in position 1 (e.g., see the arm position in FIG. 18). The arm can include any number of positions, e.g., 1-10 positions or 1-3 positions or 1-2 positions. FIGS. 18-20 show the arm in three different positions. The user hits start again and the device runs at a second frequency for a predetermined amount of time. The protocol can be divided into steps where, at each step, varied outputs are predetermined or specified.

In a preferred embodiment, the device 400 includes a housing 101, an electrical source 114, a motor 406 positioned in the housing 101, a switch 405 (which can be any of the touch screen 409, rocker button 447, button 404 or any other switch or button) for activating the motor 406, and a routine controller 630. The device 400 is configured to mate with an attachment 628. The attachment can be, for example, the attachment 628 shown in FIG. 18. The attachment is affixed to the male connector 410 so that the shaft or push rod assembly 208 moves the attachment reciprocally in accordance with a specified amplitude. For example, the amplitude is depicted in FIGS. 22A and 22B, where FIG. 22A shows the attachment at a maximum extended position and FIG. 22B shows the attachment at a minimum extended position. The distance between maximum and minimum extended positions can, in an embodiment, define the amplitude.

The attachment 628 can be a variety of attachments configured to provide therapeutic relief to specified portions of the body. For example, the attachment 628 can be a standard ball (see U.S. patent application Ser. No. 29/677,157, the entirety of which is incorporated herein by reference) attachment targeted for overall use on both large and small muscle groups. The attachment 628 can be a cone attachment (see U.S. Pat. No. D849,261, the entirety of which is incorporated herein by reference) for pinpoint muscle treatment, trigger points, and small muscle areas like the hands and feet. The attachment 628 can also be a dampener attachment (see U.S. patent application Ser. No. 29/676,670, the entirety of which is incorporated herein by reference) used for tender or bony areas, but also for overall uses. The attachment 628 can be a wedge attachment (see U.S. Pat. No. D845,500, the entirety of which is incorporated herein by reference) for use on shoulder blades and IT bands, used for "scraping" and "flushing" motions that help to flush lactic acid out of muscles. The attachment 628 can be a large ball (see U.S. patent application Ser. No. 29/677,016, the entirety of which is incorporated herein by reference) for large muscle groups like glutes and quads. The attachment 628 can be a thumb attachment (see U.S. Pat. No. D850,639, the entirety of which is incorporated herein by reference) used on trigger points and the lower back. The attachment 628 can be a Supersoft™ attachment (see U.S. patent application Ser. No. 29/726,305, the entirety of which is incorporated herein by reference), designed to provide therapeutic relief to sensitive areas, including bones. One of ordinary skill in the art would recognize that the attachments described herein are non-limiting and other configurations of attachments, including varying materials and shapes, may be utilized in accordance with this embodiment. Spherical, forked, flat or other shaped attachments are all within the scope of the invention.

The routine controller 630 is configured to perform a routine in connection with one or more specified protocols. The routine controller 630 can be, for example, a microcontroller unit 701 depicted in FIG. 2. The routine controller 630 can also be a standalone microcontroller separate from the microcontroller 701. The routine controller can step through different steps of a specified protocol designed to target specified muscle groups and to provide certain therapeutic effects, as described herein.

FIG. 25 is a table showing an example of a protocol in accordance with a preferred embodiment. Protocol 1 is divided into four steps, each depicting a specified time, speed, amplitude, attachment, force, temperature, and grip. At Step 1, the device 400 is activated for 30 seconds at a speed of 1550 RPM. A routine controller 630 may be utilized to turn on the percussive massage device and implement a speed of the attachment 628 of 1550 RPM. One of ordinary skill in the art would understand that the speed of the attachment 628 is directly proportional to the speed of the motor 406. The amplitude of the percussive massage device is set to be 2 in accordance with Protocol 1. This may translate to a specified distance that an attachment 628 moves while in use, as described above. Step 1 also specifies a dampener attachment affixed to the device 400, a force of "1" be applied by the device 400, and a temperature of 21° C. be applied to the attachment.

One of ordinary skill in the art would understand that the force to be applied by the device 400 may depend upon the pressure exerted by the user in pressing the attachment onto a person's body part. As described more fully herein, the force to be applied by the device 400 may be the target force. In an embodiment where the user provides pressure to exert a particular force upon a person's body part, the routine controller 630 may adjust the output of the device 400 to ensure that the force actually applied by the attachment is the target force. The routine controller 630 may also be configured to provide feedback to the user to increase or decrease pressure on a person's body part to meet the target force. Each of these embodiments is applicable to each of the steps of a given protocol, including in Steps 2-4 below, as well as Steps 1-4 of the protocol shown in FIG. 26.

Step 1 also specifies that the device 400 is to be operated using grip 1. Grip 1, for example, may be the grip shown on the first handle portion 143 depicted in FIG. 18, otherwise referred to as a "regular" or "standard" grip. Grip 2, for example, may be the grip shown on the third handle portion 147 depicted in FIG. 19, otherwise referred to as a "reverse" grip. An "inverse" grip can also be used on third handle portion 147 (not shown). Grip 3, for example, may be the grip shown on the second handle portion 145 depicted in FIG. 20, otherwise referred to as a "base" grip.

At Step 2, Protocol 1 specifies that the device 400 be activated for 15 seconds at 2100 RPM, with an amplitude of "3", a force of "3", and a temperature of 26° C. Step 2 specifies that the small ball attachment 628 be used, and that the device 400 is to be operated using grip 1. Step 2 therefore requires that the dampener attachment in Step 1 be replaced by the small ball attachment, but specifies that the same grip is to be used.

At Step 3, Protocol 1 specifies that the device 400 be activated for 30 seconds, at 2200 RPM, with an amplitude of "1", a force of "3", and a temperature of 29° C. Step 3 specifies that the dampener attachment 628 be used, and that the device 400 is to be operated using grip 1. Step 3 therefore requires that the small ball attachment in Step 2 be replaced by the dampener attachment, but specifies that the same grip is to be used.

At Step 4, Protocol 1 specifies that the device 400 be activated for 45 seconds, at 2400 RPM, with an amplitude of "4", a force of "2", and a temperature of 32° C. Step 3 specifies that the large ball attachment be used, and that the device 400 is to be operated using grip 1. Step 3 therefore requires that the dampener attachment in Step 2 be replaced by the large ball attachment, but specifies that the same grip is to be used. It will be appreciated that Protocol 1 is provided as an example to the reader of many of the different outputs that can be changed during a myriad of treatment protocols that can be provided or developed. It will be further appreciated that any one or more of the outputs can be a part of a protocol or routine and any of the outputs discussed herein can be omitted. For example, a protocol may only include time and speed or only time speed and force, or only time, speed and grip or any other combination of the outputs described herein.

FIG. 26 is a table showing an example of a "Shin Splints" protocol in accordance with a preferred embodiment. Like Protocol 1, the Shin Splints protocol is divided into four steps, each depicting a specified time, speed, amplitude, attachment, force, temperature, and grip, but also specifying a particular arm position and body part to which to apply the attachment. At Step 1, the device 400 is activated for 1 minute at a speed of 1500 RPM, with an amplitude of "1", a force of "2", and a temperature of 21° C. Step 1 specifies that the dampener attachment be used, and that the device 400 is to be operated using grip 2 ("Reverse"), to the right shin.

Step 1 also specifies the arm position 632, 634, 636 to be used is arm position 1. One of ordinary skill in the art would understand that the numbers of arm position (e.g., 1, 2, 3, 4, etc.) are predetermined arm positions intended to be used during a particular protocol. The part of the body to which the attachment 628 is to be applied is one of the factors in determining an optimal arm position. The arm position, however, may be determined by the user and is not required to otherwise implement a protocol. As shown in FIG. 18, a "standard" grip may be utilized with arm position 632 to apply to specific parts of the body. As shown in FIG. 19, a "reverse" grip may be utilized with arm position 634 to apply to specific parts of the body. As shown in FIG. 20, a "base" grip may be utilized with arm position 636 to apply to specific parts of the body. One of ordinary skill in the art would recognize that the arm position 632, 634, 636 in combination with the particular grip 143, 145, 147 may vary depending on the application. One of ordinary skill in the art will understand that setting the arm position of a device 400 depends upon the specific device. For example, certain devices may allow a user to adjust arm position while others do not. For those that do not, this step does not apply. In other embodiments, this step may be performed during execution of the steps of the particular protocol.

At Step 2, the Shin Splints protocol specifies that the device 400 be activated for 1 minute at 1500 RPM, with an amplitude of "1", a force of "2", and a temperature of 21° C. Step 2 specifies that the dampener attachment be used, and that the device 400 is to be operated using grip 2 ("Reverse"), at an arm position 1, to the left shin. Step 2 therefore uses the same attachment, grip, and arm position as Step 1, but is applied to the other shin.

At Step 3, the Shin Splints protocol specifies that the device 400 be activated for 1 minute at 2000 RPM, with an amplitude of "3", a force of "3", and a temperature of 24° C. Step 2 specifies that the dampener attachment be used, and that the device 400 is to be operated using grip 3 ("Base"), at an arm position 1, to the right calf. Step 3 therefore requires that the user change grips from "reverse" to "base" grips, but specifies that the same attachment and arm position be used.

At Step 4, the Shin Splints protocol specifies that the device 400 be activated for 1 minute at 2000 RPM, with an amplitude of "3", a force of "3", and a temperature of 24° C. Step 2 specifies that the dampener attachment be used, and that the device 400 is to be operated using grip 3 ("Base"), at an arm position 1, to the left calf. Step 2 therefore uses the same attachment, grip, and arm position as Step 1, but is applied to the other calf.

FIG. 27 is a series of flow diagrams (FIGS. 27A, 27B, 27C, 27D) showing a method 1500 of executing a routine for a percussive massage device.

Figure 27A:
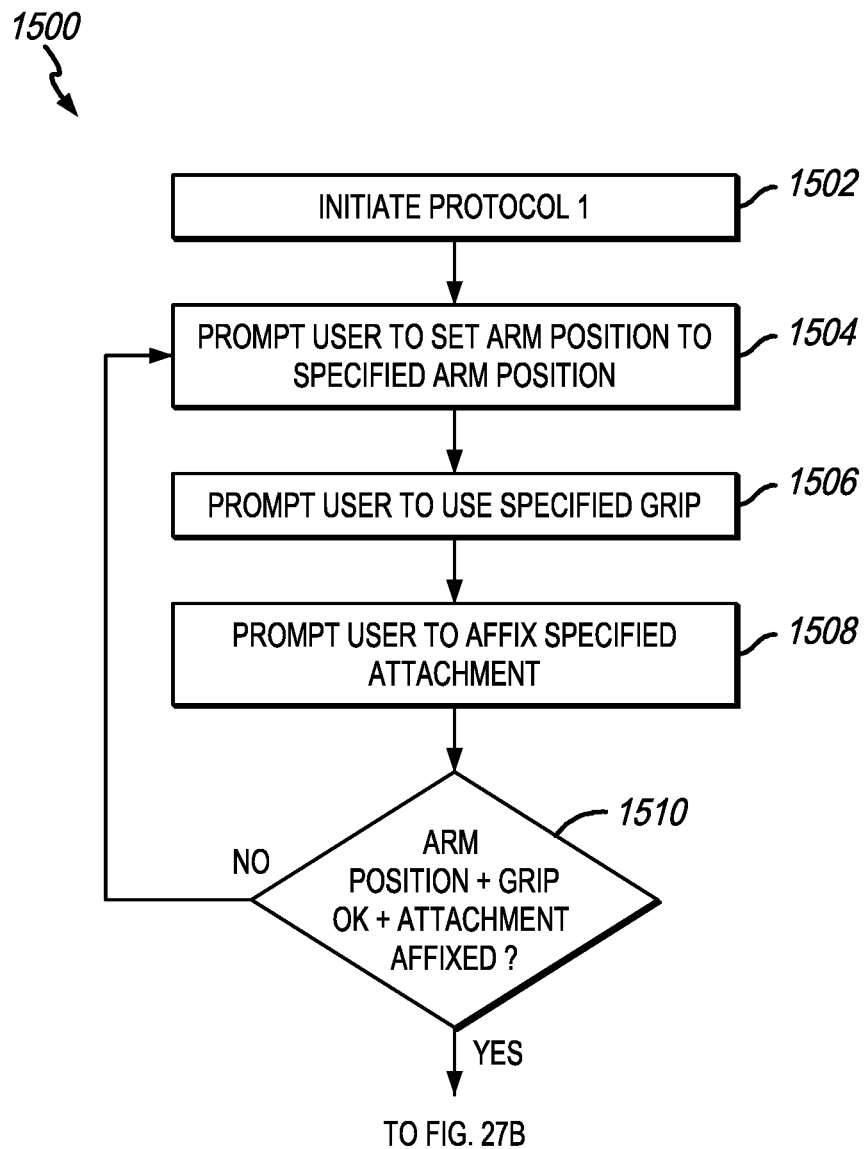
FIGS. 27A, 27B, 27C, and 27D are methods of performing a routine for a percussive massage device.

FIG. 27A is a flow diagram showing an exemplary protocol initiation. At Step 1502, Protocol 1 is initiated. Protocol 1, for example, is the Protocol 1 depicted in FIG. 25 or the "Shin Splints" Protocol depicted in FIG. 26. One of ordinary skill in the art would understand that Protocol 1 depicted in FIG. 25 does not include all of the outputs that are specified in the Shin Splints Protocol depicted in FIG. 26, and thus, not all steps of the method 1500 apply to the Protocol 1 depicted in FIG. 25.

At Step 1504, a user is prompted to set the arm position to the specified arm position 632, 634, 636. The user may be the person using the device 400 on their own body or on the body of another person. The arm position 632, 634, 636 specified in the Shin Splints Protocol is arm position 1, for example.

At Step 1506, the user is prompted to use a specified grip or handle portion 143, 145, 147 on the device 400. The grip specified in the Shin Splints Protocol is the third handle portion 147, for example. As described herein, the grip may vary depending on the particular protocol or step.

At Step 1508, the user is prompted to affix a specified attachment to the device 400. As described herein, the attachment may vary depending on the particular protocol or step.

At Step 1510, the method determines whether the arm position 632, 634, 636 and the grip position 143, 145, 147 are configured appropriately and whether the attachment 628 is affixed. Step 1510 may involve a prompt to the user by haptic feedback, application interface, or touch screen (among other types of prompts) in which the user is asked to proceed when the appropriate arm position, grip, and attachment are ready. In other embodiments, the device 400 may sense that the arm position and grip are appropriate and that an attachment is affixed before proceeding automatically. In an embodiment, Step 1510 is repeated until the arm position, grip, and attachment are ready.

Figure 27B:
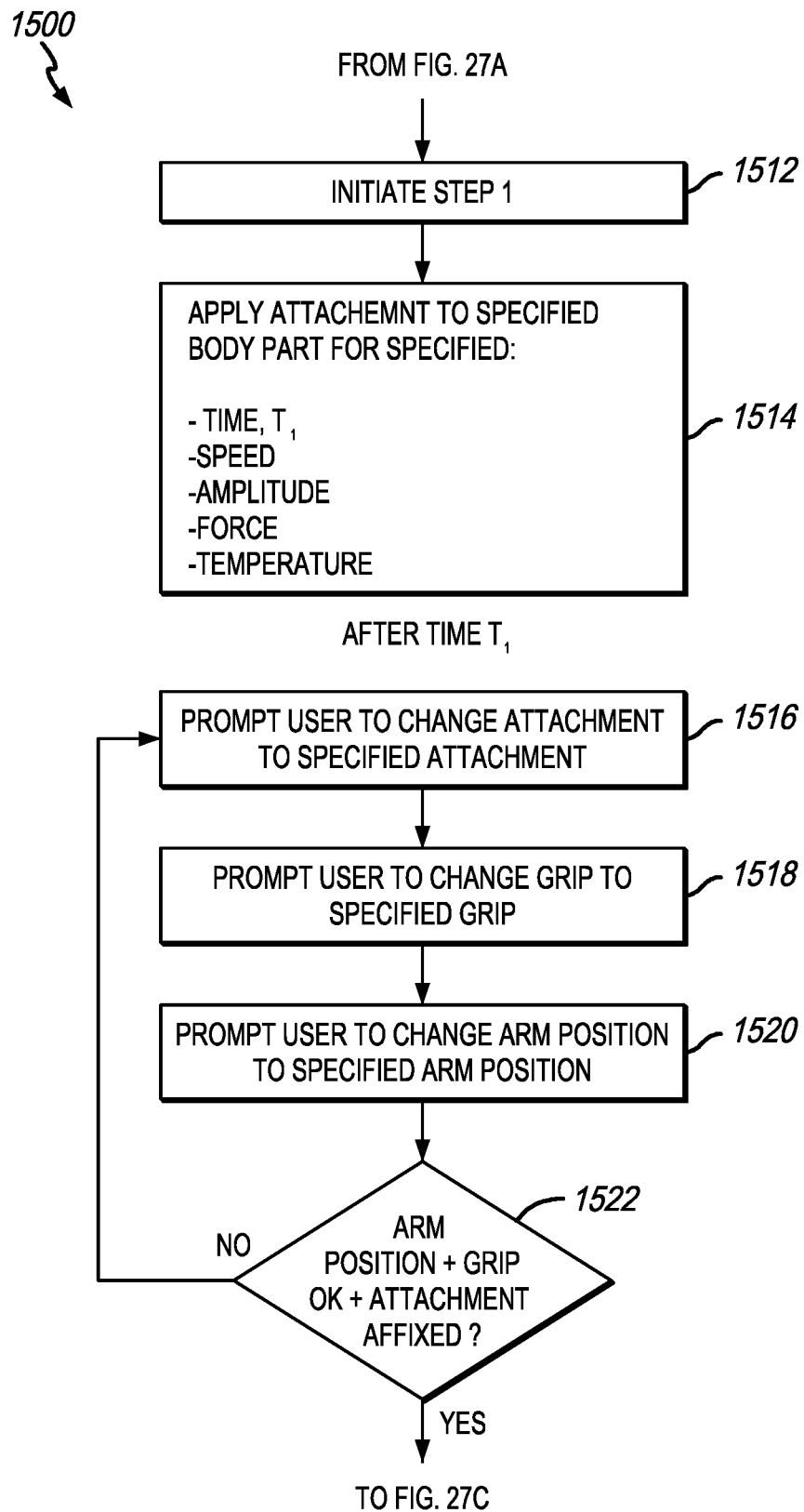

FIG. 27B is a flow diagram showing an exemplary Step 1 of the protocol, continuing the method 1500 where FIG. 27A left off.

At Step 1512, Step 1 of the protocol is initiated. Step 1, for example, is Step 1 depicted in FIGS. 25 and 26, for example.

At Step 1514, the method 1500 applies a specified time period ($T_1$) in which the device 400 is activated, a speed of the attachment, an amplitude of the attachment, a force of the attachment, and a temperature of the attachment. In an embodiment, one or more of these outputs of the device 400 are applied. These outputs may be applied by the routine controller 630. One of ordinary skill in the art would understand that a user's implementation of the device 400 on a body part is not required to apply certain of these outputs. For example, the time period, speed, amplitude, and temperature are not necessarily dependent upon a user applying pressure to a body part. On the other hand, the force applied by the attachment 628 may require a user to exert pressure on a body part for a target force (or a target force range) to be reached. Further, the temperature may vary depending on whether the attachment 628 is applied to a body part, or not, and to which body part it is applied. Thus, the temperature may need to be adjusted during application of the attachment 628 to reach a desired temperature predetermined by the protocol. In another embodiment, the temperature may be adjusted by a user.

After time period $T_1$, the user may be prompted to change the attachment 628, arm position 632, 634, 636, and/or grip position 143, 145, 147. These outputs may need to be implemented prior to the start of Step 2 of a protocol. In the Shin Splints Protocol depicted in FIG. 26, the attachment 628, arm position 632, 634, 636 and grip position 143, 145, 147 remain the same. At Step 1516, after time period $T_1$, the user is prompted to set the arm position to the specified arm position 632, 634, 636. The user may be the person using the device 400 on their own body or on the body of another person.

At Step 1518, the user is prompted to use a specified grip 143, 145, 147 on the device 400. As described herein, the grip may vary depending on the particular protocol or step.

At Step 1520, the user is prompted to affix a specified attachment 628 to the device 400. As described herein, the attachment 628 may vary depending on the particular protocol or step.

At Step 1522, the method determines whether the arm position 632, 634, 636 and the grip position 143, 145, 147 are configured appropriately and whether the attachment 628 is affixed. This step and all other like steps are optional. Step 1510 may involve a prompt to the user by haptic feedback, application interface, or touch screen (among other types of prompts) in which the user is prompted to move to the next step in the routine and/or requested to proceed when the appropriate arm position, grip, and attachment are ready. In other embodiments, the device 400 may sense that the arm position and grip are appropriate and that an attachment is affixed before proceeding automatically. In an embodiment, Step 1522 is repeated until the arm position, grip, and attachment are ready.

Figure 27C:
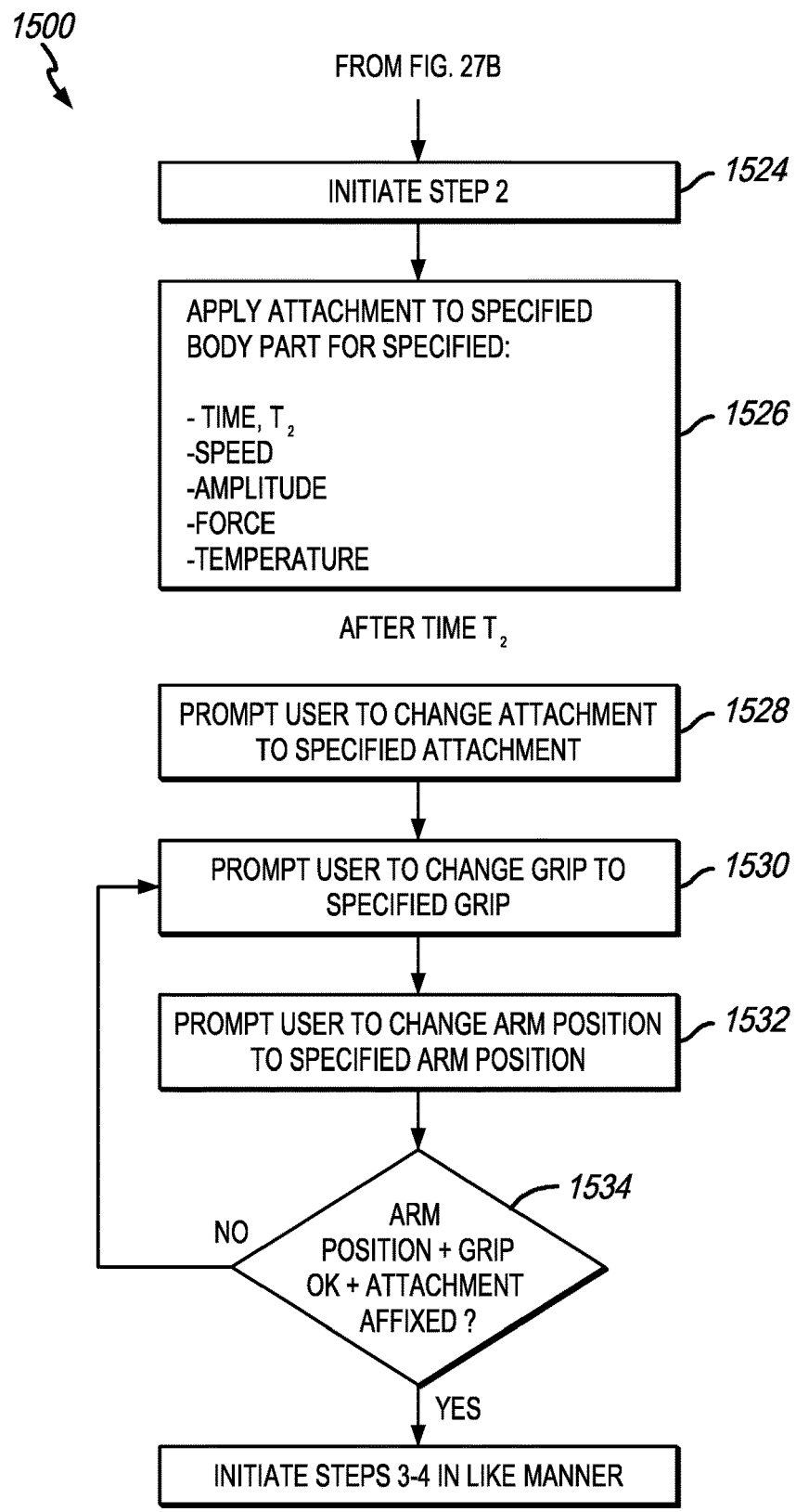

FIG. 27C is a flow diagram showing an exemplary Step 2 of the protocol, continuing the method 1500 where FIG. 27B left off.

At Step 1524, Step 2 of the protocol is initiated. Step 2, for example, is Step 2 depicted in FIGS. 44 and 45, for example.

At Step 1526, the method 1500 applies a specified time period ($T_2$) in which the device 400 is activated, a speed of the attachment, an amplitude of the attachment, a force of the attachment, and a temperature of the attachment. In an embodiment, one or more of these outputs of the device 400 are applied. These outputs may be applied by the routine controller 630. One of ordinary skill in the art would understand that a user's implementation of the device 400 on a body part is not required to apply certain of these outputs. For example, the time period, speed, amplitude, and temperature are not necessarily dependent upon a user applying pressure to a body part. On the other hand, the force applied by the attachment 628 may require a user to exert pressure on a body part for a target force to be reached. Further, the temperature may vary depending on whether the attachment 628 is applied to a body part, or not, and to which body part it is applied. Thus, the temperature may need to be adjusted during application of the attachment 628 to reach a desired temperature predetermined by the protocol. In another embodiment, the temperature may be adjusted by a user.

After time period $T_2$, the user may be prompted to change the attachment 628, arm position 632, 634, 636, and/or grip position 143, 145, 147. These outputs may need to be implemented prior to the start of Step 3 of a protocol. In the Shin Splints Protocol depicted in FIG. 26, the attachment 628 and arm position 632, 634, 636 remain the same, but the grip 143, 145, 147 is adjusted to the base grip. At Step 1528, after time period $T_2$, the user is prompted to set the arm position to the specified arm position 632, 634, 636. The user may be the person using the device 400 on their own body or on the body of another person.

At Steps 1528-1534, therefore, steps substantially the same as Steps 1516-1522 are performed. After Step 1534, Steps 3-4 are initiated in substantially the same manner as Steps 1-2. For example, Steps 3 and 4 may be Steps 3 and 4 of the Protocol 1 depicted in FIG. 25 or the Shin Splints Protocol depicted in FIG. 26. Furthermore, Step 1534 can be omitted in a device where none of the grip, arm position or attachment can be sensed by the device. In this embodiment, the given protocol simply moves from step 1 to step 2 prompting the user to make a change (but regardless of whether the user has actually made a change).

Figure 27D:
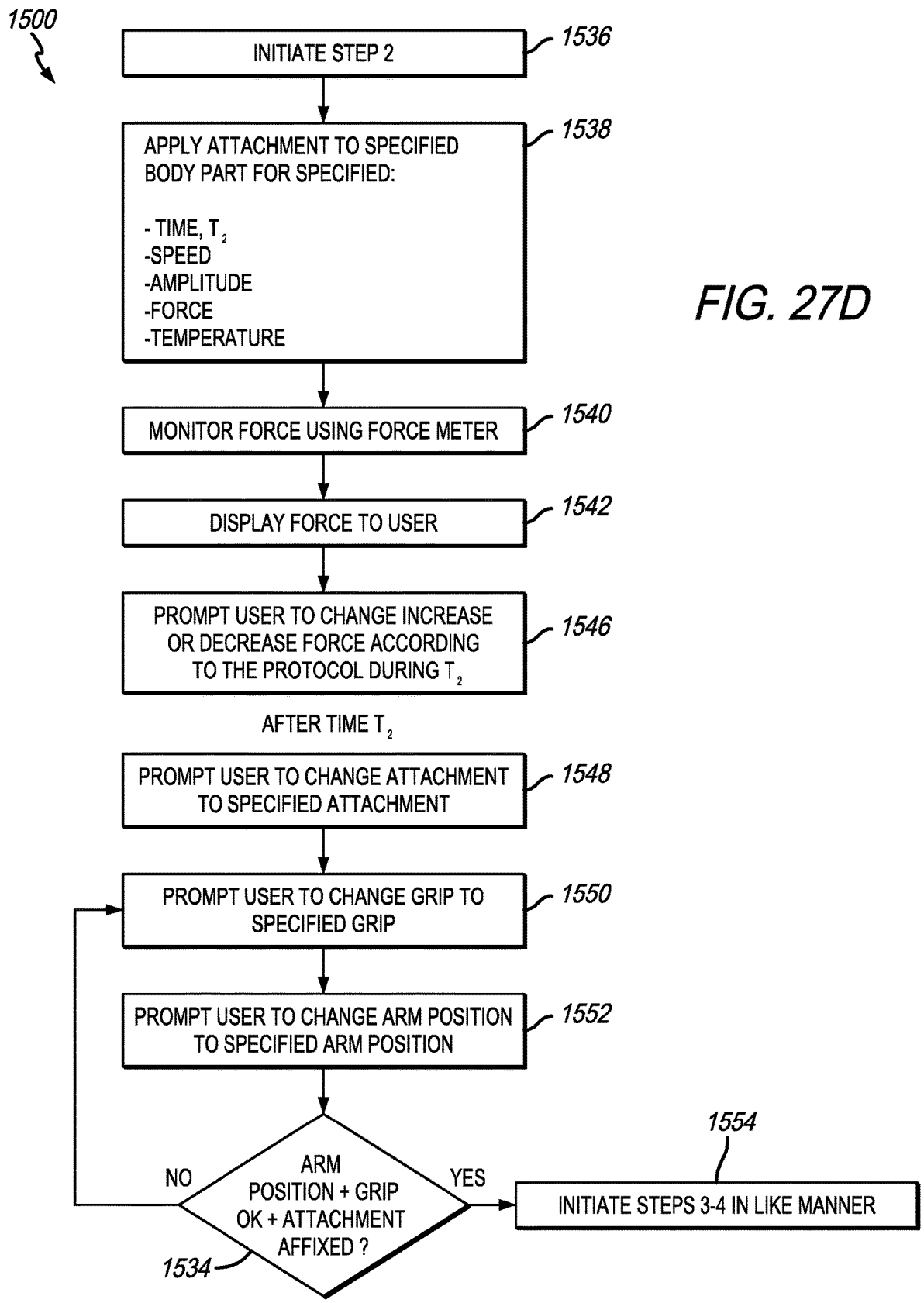

As an alternative to FIG. 27C, FIG. 27D is a flow diagram depicting an alternative Step 2 of a protocol. In the alternative Step 2, a force meter adjustment is implemented.

Steps 1536-1538 are performed substantially the same as Steps 1524-1526 in previous Step 2 above.

At Step 1540, the force being applied by the attachment 628 is monitored. In the embodiment shown in FIG. 27D, the method 1500 utilizes the force meter 400 to monitor the force actually being applied by the user.

At Step 1542, the force is displayed to the user. In an embodiment, the force is displayed on an application interface 1584 such as a graphical user interface. In other embodiments, individual use or combined use of the application interface 1584, touch screen 1582, the OLED screen 711, or the like, may be used to display the force.

Figure 29:
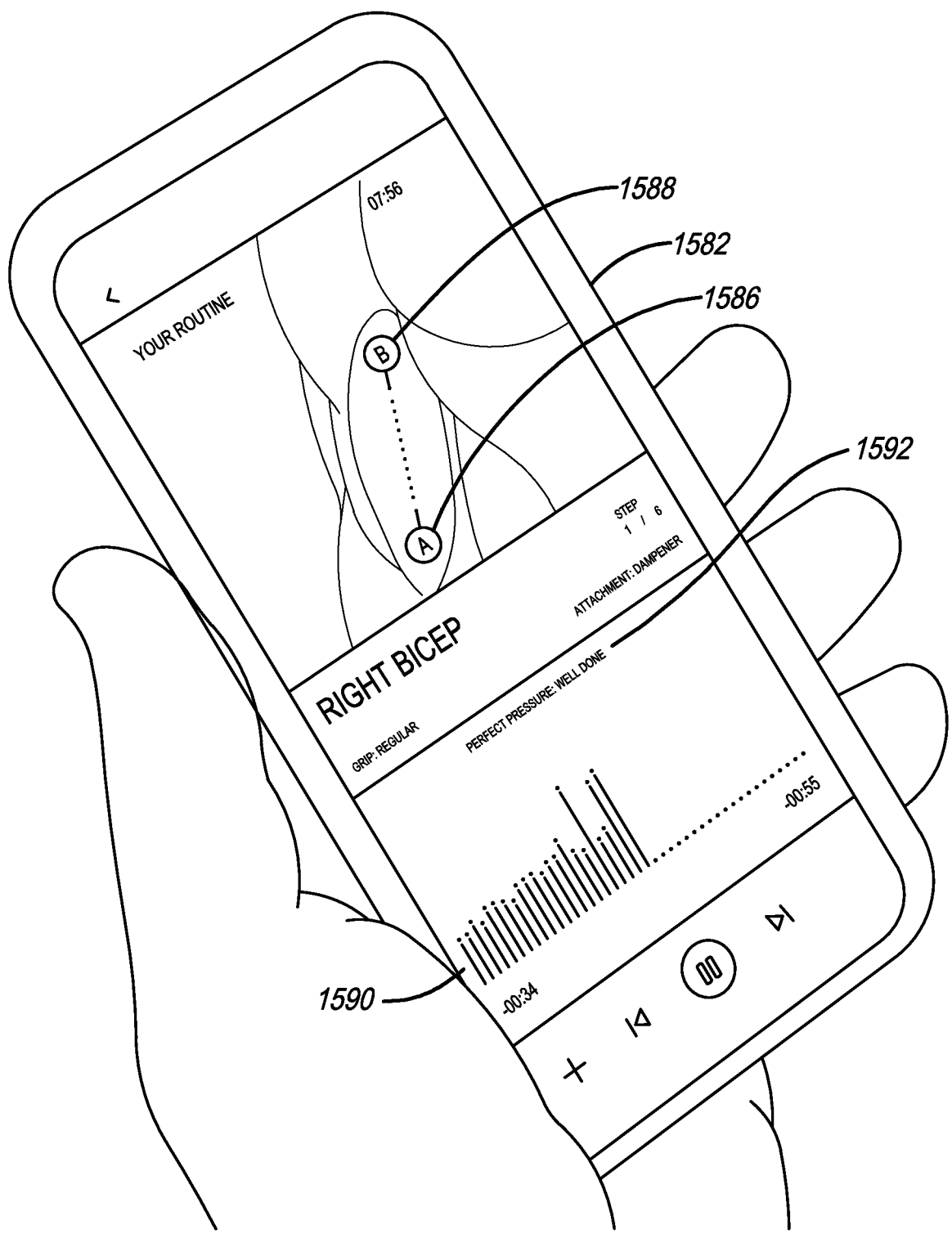
FIG. 29 is a front view of a graphical user interface showing a "Right Bicep" protocol.

At Step 1546, the user is prompted to increase or decrease the force being applied to a body part according to the specified protocol during $T_2$. FIG. 29 is a diagram showing a touch screen 1582 in accordance with an exemplary embodiment of the display of the force. A force display 1590 shows an exemplary embodiment of Step 1546. The force display 1590 shows a series of force measurements during the course of the "Right Bicep" step of a protocol. A force display prompt 1592 is used to display a message to the user such as "PERFECT PRESSURE: WELL DONE" when the force applied by the attachment 628 matches or corresponds to a target force predetermined by the protocol. In this embodiment, the force display prompt 1592 may recite "INCREASE PRESSURE" or the like if the measured force applied by the attachment 628 is lower than the target force predetermined by the protocol. Consequently, if the measured force applied by the attachment 628 is higher than the target force predetermined by the protocol, then the force display prompt 1592 may recite "DECREASE PRESSURE" or the like. The user may then adjust the pressure the user is exerting on the body part to either increase pressure or decrease pressure according to the force display prompt 1592 so that the measured force is equivalent or substantially equivalent to the target force.

After time period $T_2$, the user may be prompted to change the attachment 628, arm position 632, 634, 636, and/or grip position 143, 145, 147. These outputs may need to be implemented prior to the start of Step 3 of a protocol. In the Shin Splints Protocol depicted in FIG. 26, the attachment 628 and arm position 632, 634, 636 remain the same, but the grip 143, 145, 147 is adjusted to the base grip. At Step 1528, after time period $T_2$, the user is prompted to set the arm position to the specified arm position 632, 634, 636. The user may be the person using the device 400 on their own body or on the body of another person.

At Steps 1548-1552, therefore, steps substantially the same as Steps 1516-1522 are performed. After Step 1534, Steps 3-4 are initiated in substantially the same manner as Steps 1-2. For example, Steps 3 and 4 may be Steps 3 and 4 of the Protocol 1 depicted in FIG. 25 or the Shin Splints Protocol depicted in FIG. 26.

Figure 28:
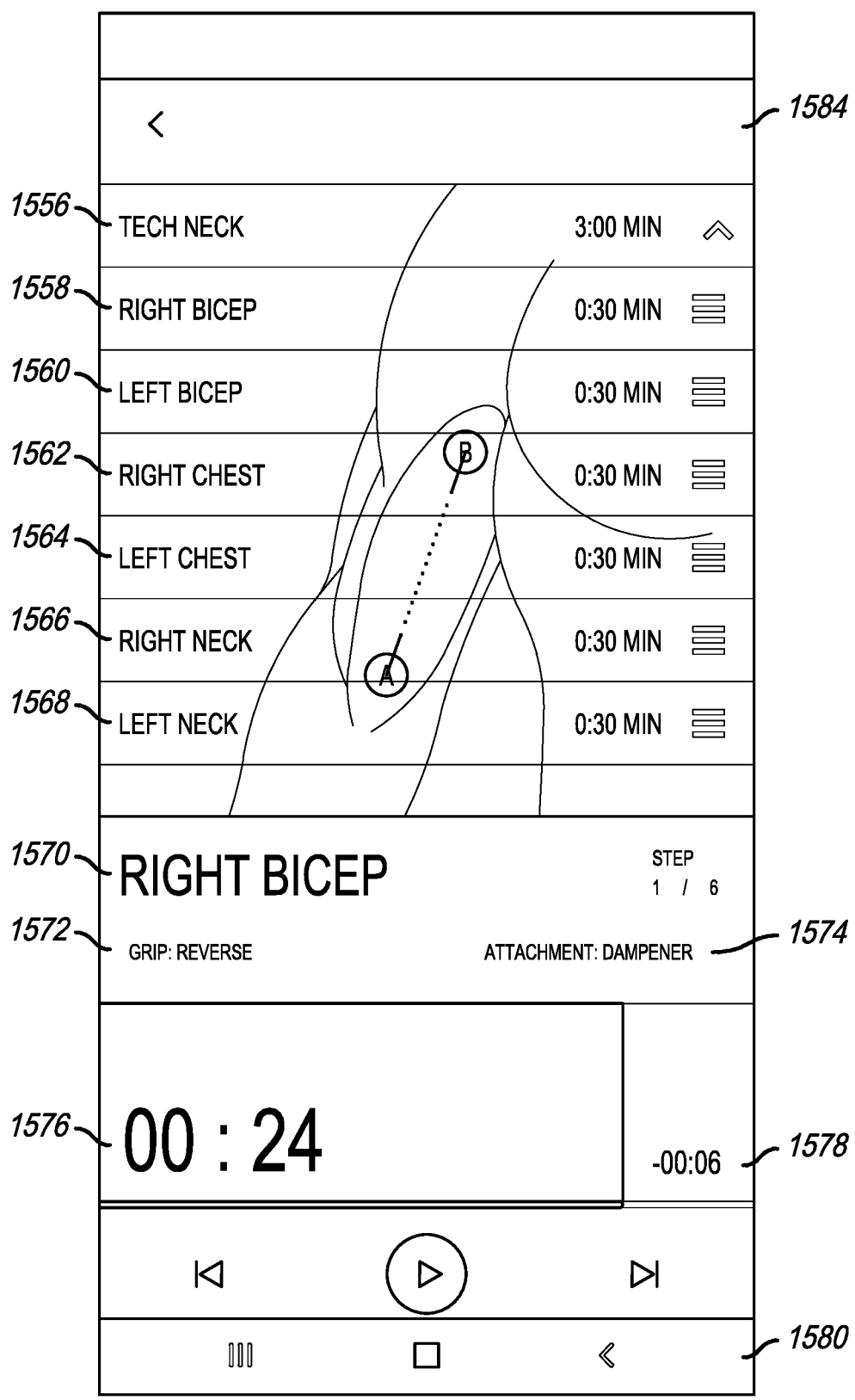
FIG. 28 is a front view of a graphical user interface showing a "Tech Neck" protocol.

FIG. 28 is a diagram in accordance with an exemplary embodiment of an application interface 1584. At the top of the interface 1584, a protocol field 1556 is displayed to the user. In this embodiment, the protocol field 1556 is "TECH NECK." The protocol title 1556 also shows the overall time period of the protocol.

The next portion of the interface 1584 shows step fields 1558-1568 of the protocol that are displayed to the user. In this embodiment, the step fields identify the title of the step and time period of the step. For example, step field 1558 is titled "RIGHT BICEP" (where the treatment will be provided) and the time period of activation is "0:30 MIN."

The interface 1584 also includes a current step field 1570 that identifies the current step title 1570, a grip title display 1572, and an attachment title display 1574.

The interface 1584 also includes a time display 1576 and a time remaining display 1578 to show the user how much time has occurred during that step and the time remaining in that step. Finally, the interface 1584 includes a control field 1580 to play, skip back, and skip forward from step to step.

As described above, FIG. 28 shows a touch screen 1582 on a mobile device. The touch screen 1582 displays a graphic depicting a starting point 1586 "A" and an end point 1588 "B" (thereby defining a treatment path) showing the user where to apply the attachment 628 to the specified body part. In FIG. 28, the display instructs the user to move the attachment from the lower portion of the right bicep to the upper portion of the right bicep (the treatment path) during the current step. In some embodiments, during a single step, the user may be prompted or shown on the graphical user interface more than one treatment path (or a first treatment path and a second treatment path) on the same body part/muscle or on different body parts/muscles. For example, during the right bicep step, the user may be prompted to first move the device along the path shown in FIG. 28, but, during the same 30 second step may also be prompted or shown a path that is parallel to the path shown in FIG. 28.

Figure 30:
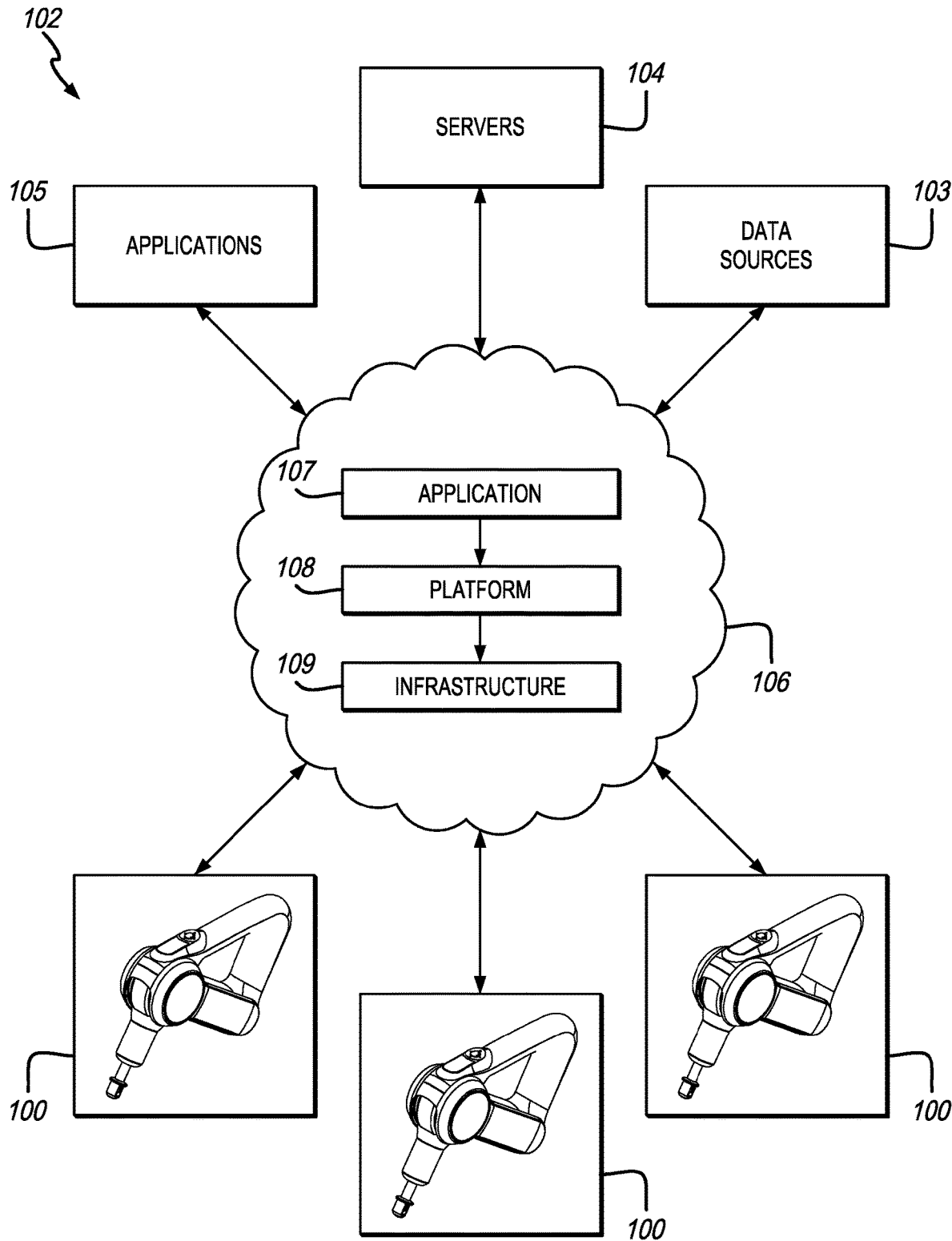
FIG. 30 is a system block diagram showing structure of a percussive therapy system.
Figure 31:
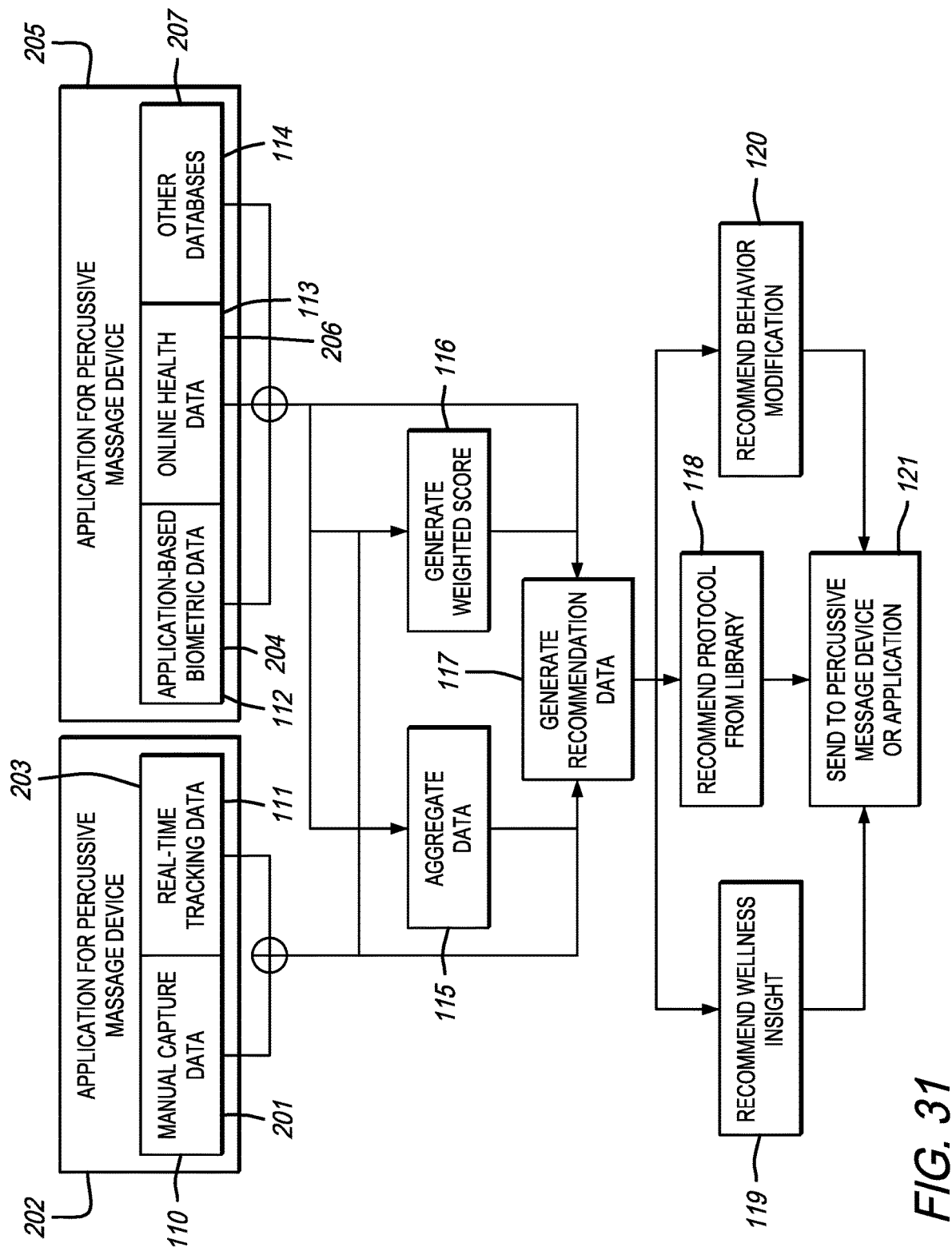
FIG. 31 is a flow diagram depicting a method of providing therapeutic effect using a percussive massage device utilizing the Intelligence Engine in accordance with an embodiment of the present invention.

FIGS. 30-31 depict an intelligence engine system and method in accordance with preferred embodiments of the present invention.

The Intelligence Engine is an artificial intelligence (AI) solution that is designed to personalize use of wellness technologies to optimize the therapeutic benefits of them relative to a user's learnt needs and preferences. The intelligence engine is modeled to prescribe evidence-based recommendations for a number of wellness technologies and behaviors. Of primary importance are behaviors associated with a percussive massage device 400. Percussive therapy "routines" can be broken down into "steps" associated with key components of application which elicit specific physiological and neurological outcomes.

For example, a routine may be a protocol made up of multiple steps designed to guide the application of a device 400 on different areas of a user's body. A routine or protocol may consist of a total number of steps and individual step duration (determines overall routine duration), the frequency of routine application by the user, and the order of steps.

For example, a step may be a component of a routine which dictates the specific application of percussive therapy using the device 400 to a single area of the body. The step may include an area of application, a duration of application to that area, a force applied during application, an attachment used during application, and a frequency setting (motor speed) used during application.

The Intelligence Engine utilizes multiple input data to provide data mapping. Such inputs include data from manual capture, application tracking/analytics, and integrations with third party data sources to elicit specific responses from a multidimensional rule engine which results in outputs related to changes to routines and steps.

For example, the input data may include user demographics, including biological sex, age, height, and weight. The input data may include activity type, volume (e.g., distance, time, repetitions, etc.), intensity (e.g., pace, load, weigh-per-type, etc.), trends (e.g., changes in activity dimensions over time). The input data may further include temporal data such as absolute time or relative time, that is, relevant to a determined "event." The input data may further include percussive therapy analytics including duration of use (global and local on body) and frequency of use (global and local on body). The input data may further include force, frequency, and attachment metrics for variables above associated with the device 400. The input data may further include biometric data including heart rate (HR) (e.g., resting, sleep, recovery, etc.), heart rate variation (HRV) (e.g., resting, sleep), sleep metrics (e.g., onset, latency, disturbances, score, duration, etc.), temperature (e.g., body temperature of a user), and imaging data (e.g., thermography, ultrasound, x-ray, etc.). The input data may also include weighted determination scores based on recovery, well-being (e.g., wellness), and/or behavior (e.g., based on variety of the input data described herein). One of ordinary skill in the art would recognize that other input data not mentioned herein are within the scope of the present invention.

The Intelligence Engine also provides output data to the device 400 (or devices) or the user (or users). The output data itself may be input data, depending on the application. For example, a particular output data relating to a particular device 400 or a particular user may be aggregated and the aggregated data may be utilized to develop further modification of other output recommendations. In an embodiment, the aggregation of large datasets from users within segmented populations can be used to discover associations and trends between behaviors and outcomes. These can then be used to modify the rules engines to help optimize the behavioral outcomes of users relative the therapeutic benefits of using percussive therapy.

The output data may include recommendation data including recommended protocols to the device 400 or the user. The output data may include changes in the user experience that occur as a result of the input data described herein.

For example, the output data may include a dynamic user experience including recommended routines, re-prioritization and sorting of libraries, and highlighted content. The output data may further include "bespoke" routine synthesis including creation of unique routine for a particular user and modification of steps within a routine (e.g., body part inclusion/exclusion, step duration, force/frequency/attachment recommendations, etc.). The output data may further include personalized insights including subject matter such as wellness/well-being, using, for example, biometric data, behavioral characteristics, using, for example, device analytics and third party data sources, and/or a combination of biometric data and behavioral characteristics. The output data may further include notifications to the user or the device 400, including recommended routine(s), changes to routine(s), and/or behavior recommendation(s). One of ordinary skill in the art would recognize that other data outputs not mentioned herein are within the scope of the present invention.

FIG. 30 is a system block diagram showing structure of a percussive therapy system 102. The percussive therapy system 102 includes one or more devices 100, data sources 103, servers 104, applications 105, and a cloud 106.

The data sources 103 include, for example, online or cloud-based data sources of health and wellness information. The health and wellness information may be aggregated data from a number of unorganized sources upon which statistical analysis can be done. The data sources 103 may also include biometric information from wearable biometric devices, such as, for example, Biostrap wearable devices, Apple® wearable devices, and the like. The data sources 103 may include information from Apple's Apple Health application, MyFitnessPal application, and the like.

The servers 104 and applications 105 are well known to one of ordinary skill in the art. The servers 104 may include structure configured to facilitate processing and data storage and transfer. The applications 105 may be standalone applications configured to be executed on a smart device, a standalone computer, a laptop, an entertainment center, or other computing devices.

In this embodiment, the cloud 106 includes an application 107, a platform 108, and an infrastructure 109. For example, the application 107 may include a variety of applications configured to execute all or portions of the functions of an intelligence engine in connection with the platform 108 and the infrastructure 109. One of ordinary skill in the art would understand that the cloud 106 and its constituents therein is only one way to depict a cloud-based computing system and there are a variety of other ways to depict the same without departing from the scope of the present invention.

FIG. 31 is a flow diagram depicting a method of providing therapeutic effect using a percussive massage device utilizing the Intelligence Engine in accordance with an embodiment of the present invention.

At Step 110, manual capture data 201 is generated. The manual capture data 201 is, for example, data input via the touch screen 1582 of FIG. 29. An application 202 running on a smart device associated with the touch screen 1582 may prompt a user to input answers to questions regarding health, wellness, or other parameters useful to provide recommendation data to the user. Alternatively, though not shown in connection with FIG. 31, a user may input data directly into the device 400, which may then be transferred wirelessly to be used by the Intelligence Engine.

At Step 111, real-time tracking data 203 is generated. In the embodiment depicted in FIG. 31, an application 202 configured to wirelessly connect to the device 400 monitors and stores real-time tracking data of a user's use of the device 400. In an embodiment, the application 202 transmits the real-time tracking data to a cloud-based computing system such as that shown in FIG. 30. In other embodiments, a standalone computing system may be utilized.

At Step 112, application-based biometric data 204 is provided via one of a remote data sources 205. At Step 113, online health data 206 is provided via another one of the remote data sources 205. At Step 114, data from other databases 207 is provided via another one of the remote data sources 205. One of ordinary skill in the art would understand that the remote data sources 205 may include the data sources 103.

One of ordinary skill in the art would understand that the various input data described herein may be substituted for the particular input data described in connection with FIG. 31 without departing from the scope or spirit of the present invention.

At Step 115, all or portions of the manual capture data 201, real-time tracking data 203, application-based biometric data 204, online health data 206, and data from the other databases 207 are aggregated. One of ordinary skill in the art would understand the methodology for data aggregation, and as more fully described herein.

At Step 116, a weighted score is generated based on all or portions of the manual capture data 201, real-time tracking data 203, application-based biometric data 204, online health data 206, and data from the other databases 207. The weighted score may include a recovery determination score, a wellness determination score, and a behavior determination score. As an example, the recovery determination score includes a determination of how long a user's HB returned to a restorative state. Depending on the application's parameters, the score could, for example, determine that a Recovery Score is Poor, as described more fully below in Table 1. As another example, a wellness determination score includes a determination of dietary intake and trends to determine an overall wellness score. Depending on the application's parameters, the score could, for example, determine that a data input regarding dietary intake was within predetermined parameters, thereby increasing the user's wellness determination score. As another example, a behavior determination score includes a determination of sleep metrics and trends to determine an overall behavior determination score. Depending on the application's parameters, the score could, for example, determine that a Sleep Metrics score was Poor, as described more fully below in Table 1.

At Step 117, recommendation data is generated based on all or portions of (1) the aggregated data (2) the weighted score and (3) all or portions of the manual capture data 201, real-time tracking data 203, application-based biometric data 204, online health data 206, and data from the other databases 207. These data may all be combined to generate the recommendation data. Alternatively, only a weighted score is utilized to generate the recommendation data. In yet another alternative, only real-time tracking data 201 is utilized to generate the recommendation data. One of ordinary skill in the art would understand the various data inputs are fluid and may be utilized based on desired parameters for optimum health and wellness.

At Step 118, a recommended protocol is determined as part of the recommendation data. The recommended protocol is, in an embodiment, obtained from a library of protocols. For example, FIGS. 26-29 depict various protocols that may be obtained from the library of protocols. In another embodiment, the recommended protocol is synthesized from available data, i.e., a "bespoke" routine synthesis suitable for a particular user.

At Step 119, a wellness insight is recommended as part of the recommendation data. The wellness insight, for example, may be based on the weighted score that determines that the user's dietary intake is poor and thus, would provide an insight that may assist the user to modify their dietary intake. Other examples are within the scope of the present invention.

At Step 120, a behavior modification is recommended as part of the recommendation data. The behavior modification, for example, may be based on the weighted score that determines that a user's Sleep Metrics are Poor, thereby prompting a behavior modification notification to the user to alert the user about his or her poor sleep habits.

At Step 121, one or more of the recommended protocol, wellness insight, or behavior modification is provided to the device 400 or the application 202. Preferably, the user of the device 400 is notified in accordance with the recommendation data.

Table 1 below provides an example of input data and output data for a particular scenario in accordance with a preferred embodiment.

| INTELLIGENCE ENGINE | |
|---|---|
| INPUT DATA | OUTPUT DATA |
| Female | Modification of steps in routines |
| 57 | Modification of steps in routines |

-continued

| INTELLIGENCE ENGINE | |
|---|---|
| INPUT DATA | OUTPUT DATA |
| Activity = Run | Prioritization of specific routines and personalized notifications |
| Duration = 51 minutes | Prioritization of specific routines and the modification of steps within them |
| Distance = 8 miles | Prioritization of specific routines and the modification of steps within them |
| Trends = X % Faster and longer than normal | Prioritization of specific routines and the modification of steps within them |
| Time = Evening | Prioritization of second series of routines and personalized notifications |
| Time = Within 2 hours of activity completion | Prioritization of specific routines, and personalized notifications |
| Recent Percussive Therapy = Short + Infrequent | Modification of steps in routines and highlighting of insights |
| Recovery Score = Poor | Prioritization of specific routines, the modification of steps within them, personalized notifications, and highlighting of insights |
| Sleep Metrics = Poor | Prioritization of specific routines, the modification of steps within them, personalized notifications, and highlighting of insights |

Recent research in sports science has focused on goals to (1) better understand the effects of percussive therapy on biometrics collected from a wearable technology, and (2) to provide objective quantitative evidence for the effects of using a connected percussive therapy device guided by an application to elicit positive benefits.

The research study included 75 healthy 20-50 year olds, exercising a minimum of three times per week for greater than 30 minutes. The research study design was a free-living design where the following parameters were controlled. During weeks 1+2 normal life, where users measure everything using wearable biometric sensor. During weeks 3+4 same as 1+2 but use percussive massage device (1) after user exercise following specific application recovery routines for the activity generated from recommendation data, and (2) 30 minutes' use before bed based on specific application sleep routine according to recommendation data. During week 5, weeks 1+2 are repeated with no percussive massage device to assess the potential lasting effects of using percussive therapy.

Chronic effects from the research study include that a wearable biometric sensor score revealed that 67% of participants improved their recovery score, the average improvement was 9%, a maintained benefit (8% improvement from baseline) during week 5, and the greatest improvement of 91%. The effects also revealed that 64% of participants improved HRV, for an average increase of 6% (median RMSSD), and a maintained benefit during week 5. The sleep latency effects revealed that 87% of participants improved sleep latency, for an average improvement of 24% (fell asleep approximately 4.25 minutes faster), and a benefit increased to average improvement of 30% during week 5. The sleep efficiency effects revealed that 70% of participants improved sleep efficiency, for an average improvement of 2%. The sleep awakenings effects revealed that 73% of participants experienced less awakenings, for an average improvement of 7% (0.38 less awakenings per evening). A sleep score revealed that 56% of participants improved sleep score, for an average improvement of 4%, with a benefit increased to an average improvement of 5% during week 5, with a greatest improvement of 65%.

Acute effects from the research study include that for resting HR, 75% of participants decreased RHR, and 4% of participants decreased RHR by 2.65 bpm on average. The HRV effects included that 78% of participants increased HRV, and 25% of participants increased HRV by 12.43 ms on average.

Accordingly, recent research tends to suggest that use of a wearable biometric sensor in connection with a device 400, utilizing aspects of the Intelligence Engine disclosed herein, results in improved health and wellness for the user.

Although the operations of the method(s) herein are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description of the Preferred Embodiments using the singular or plural number may also include the plural or singular number respectively. The word "or" in reference to a list of two or more items, covers all of the following interpretations of the word: any of the items in the list, all of the items in the list, and any combination of the items in the list.

The above-detailed description of embodiments of the disclosure is not intended to be exhaustive or to limit the teachings to the precise form disclosed above. While specific embodiments of and examples for the disclosure are described above for illustrative purposes, various equivalent modifications are possible within the scope of the disclosure, as those skilled in the relevant art will recognize. Further, any specific numbers noted herein are only examples: alternative implementations may employ differing values, measurements or ranges.

Although the operations of any method(s) disclosed or described herein either explicitly or implicitly are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

The teachings of the disclosure provided herein can be applied to other systems, not necessarily the system described above. The elements and acts of the various embodiments described above can be combined to provide further embodiments. Any measurements or dimensions described or used herein are merely exemplary and not a limitation on the present invention. Other measurements or dimensions are within the scope of the invention.

Any patents and applications and other references noted above, including any that may be listed in accompanying filing papers, are incorporated herein by reference in their entirety. Aspects of the disclosure can be modified, if necessary, to employ the systems, functions, and concepts of the various references described above to provide yet further embodiments of the disclosure.

These and other changes can be made to the disclosure in light of the above Detailed Description of the Preferred Embodiments. While the above description describes certain embodiments of the disclosure, and describes the best mode contemplated, no matter how detailed the above appears in text, the teachings can be practiced in many ways. Details of the system may vary considerably in its implementation details, while still being encompassed by the subject matter disclosed herein. As noted above, particular terminology used when describing certain features or aspects of the disclosure should not be taken to imply that the terminology is being redefined herein to be restricted to any specific characteristics, features or aspects of the disclosure with which that terminology is associated. In general, the terms used in the following claims should not be construed to limit the disclosures to the specific embodiments disclosed in the specification unless the above Detailed Description of the Preferred Embodiments section explicitly defines such terms. Accordingly, the actual scope of the disclosure encompasses not only the disclosed embodiments, but also all equivalent ways of practicing or implementing the disclosure under the claims.

While certain aspects of the disclosure are presented below in certain claim forms, the inventors contemplate the various aspects of the disclosure in any number of claim forms. For example, while only one aspect of the disclosure is recited as a means-plus-function claim under 35 U.S.C. § 112, ¶6, other aspects may likewise be embodied as a means-plus-function claim, or in other forms, such as being embodied in a computer-readable medium. (Any claims intended to be treated under 35 U.S.C. § 112, ¶6 will include the words "means for"). Accordingly, the applicant reserves the right to add additional claims after filing the application to pursue such additional claim forms for other aspects of the disclosure.

Accordingly, although exemplary embodiments of the invention have been shown and described, it is to be understood that all the terms used herein are descriptive rather than limiting, and that many changes, modifications, and substitutions may be made by one having ordinary skill in the art without departing from the spirit and scope of the invention.

What is claimed is:

1. A percussive therapy system comprising:
    a percussive massage device comprising a network interface,
    an intelligence engine configured to receive manual capture data and real-time tracking data from the percussive massage device, receive remote data from at least one remote data source, and generate recommendation data comprising a recommended protocol to be performed by the percussive massage device,
    wherein the recommendation data is generated from at least one of demographic data, activity data comprising prior use of the percussive massage device, temporal data comprising timing of use of the percussive massage device, analytics data corresponding to use of the percussive massage device, and biometric data, received from the manual capture data, the real-time tracking data, and the remote data, wherein the recommendation data comprises at least one of a behavior modification recommendation and a wellness insight, wherein the recommendation data is generated based at least in part on first aggregated data from at least one of the demographic data, the activity data, the temporal data, the analytics data, and the biometric data of a user stored on a remote server, wherein the recommendation data is generated based on second aggregated data from the remote data comprising datasets from users within segmented populations to discover associations between behaviors and behavioral outcomes to optimize the behavior modification recommendation, wherein the recommendation data is generated from a weighted scoring determination comprising at least one of a recovery determination score, a wellness determination score, and a behavior determination score, wherein the recommended protocol comprises at least two percussive massage device routines, each comprising a series of steps configured to be performed in a predetermined order, and wherein, based on the weighted scoring determination, the first aggregated data, and the second aggregated data, one or more of the at least two percussive massage device routines is prioritized, and one or more of the series of steps of the at least two percussive massage device routines is modified to improve the recovery determination score, the wellness determination score, and the behavior determination score.

2. The percussive therapy system of claim 1 wherein the recommendation data is provided to the percussive massage device.

3. The percussive therapy system of claim 1 wherein the recommendation data comprises a user notification of at least one of the recommended protocol, a change to the recommended protocol, and a behavior recommendation.

4. The percussive therapy system of claim 1 wherein the demographic data comprises at least one of a biological parameter of a user, an age of the user, a height of the user, and a weight of the user.

5. The percussive therapy system of claim 1 wherein the activity data comprises at least one of a type of exercise activity, a volume of the exercise activity, an intensity of the exercise activity, and a trend in activity parameters over time.

6. The percussive therapy system of claim 1 wherein the temporal data comprises at least one of an absolute time of an exercise routine of a user and a relative time of the exercise routine to a predetermined event.

7. The percussive therapy system of claim 1 wherein the analytics data comprises at least one of a duration of use, a frequency of use, a force of use, and an attachment use of the percussive massage device.

8. The percussive therapy system of claim 1 wherein the biometric data comprises at least one of a heart rate of a user, a heart rate variation of the user, sleep metrics of the user, a temperature of the user, and imaging data comprising at least one of a thermographic image of a user, an ultrasound of the user, and an x-ray image of the user.

9. The percussive therapy system of claim 1 wherein the recovery determination score is improved by decreasing resting heart rate.

10. The percussive therapy system of claim 1 wherein the recovery determination score is improved by increasing heart rate variation.

11. The percussive therapy system of claim 1 wherein the wellness determination score is improved by decreasing sleep latency.

12. The percussive therapy system of claim 1 wherein the wellness determination score is improved by decreasing sleep awakenings.

13. The percussive therapy system of claim 1 wherein a force applied by the percussive massage device in at least one step of the one or more of the series of steps of the at least two percussive massage device routines is configured to be reduced when applied to a specified body part of the user.

14. The percussive therapy system of claim 1 wherein a duration of application of the percussive massage device in at least one step of the one or more of the series of steps of the at least two percussive massage device routines is configured to be reduced when applied to a specified body part of the user.

15. The percussive therapy system of claim 1 wherein a specified attachment to be applied to a user's body part by the percussive massage device is configured to be applied in at least one step of the one or more of the series of steps of the at least two percussive massage device routines.

16. The percussive therapy system of claim 1 wherein a duration of the one or more of the series of steps of the at least two percussive massage device routines of the percussive massage device is configured to be reduced when applied to a specified body part of the user.

17. A method of providing therapeutic effect using a percussive massage device, the method comprising the steps of:

receiving manual capture data and real-time tracking data of the percussive massage device, receiving remote data inputs from at least one remote data source, aggregating the manual capture data, the real-time tracking data, and the remote data inputs, each comprising at least one of demographic data, activity data comprising prior use of the percussive massage device, temporal data comprising timing of use of the percussive massage device, analytics data corresponding to use of the percussive massage device, and biometric data to obtain first aggregated data, aggregating datasets from users within segmented populations to discover associations between behaviors and behavioral outcomes to optimize a behavior modification recommendation provided to a user to obtain second aggregated data, generating a weighted scoring determination comprising at least one of a recovery determination score, a wellness determination score, and a behavior determination score, generating recommendation data from the first and second aggregated data comprising a recommended protocol to be performed by the percussive massage device, wherein the recommended protocol comprises at least two percussive massage device routines, each comprising a series of steps configured to be performed in a predetermined order, and prioritizing one or more of the at least two percussive massage device routines based on the weighted scoring determination, the first aggregated data, and the second aggregated data, and modifying one or more of the series of steps of the at least two percussive massage device routines to improve the recovery determination score, the wellness determination score, and the behavior determination score.

* * * * *